(12) United States Patent
Klimov et al.

(10) Patent No.: US 12,175,367 B2
(45) Date of Patent: Dec. 24, 2024

(54) PREDICTING DCIS RECURRENCE RISK USING A MACHINE LEARNING-BASED HIGH-CONTENT IMAGE ANALYSIS APPROACH

(71) Applicant: Georgia State University Research Foundation, Inc., Atlanta, GA (US)

(72) Inventors: Sergey Klimov, Roswell, GA (US); Yi Jiang, Atlanta, GA (US); Arkadiusz Gertych, El Segundo, CA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 611 days.

(21) Appl. No.: 17/415,260

(22) PCT Filed: Dec. 16, 2019

(86) PCT No.: PCT/US2019/066629
§ 371 (c)(1),
(2) Date: Jun. 17, 2021

(87) PCT Pub. No.: WO2020/131746
PCT Pub. Date: Jun. 25, 2020

(65) Prior Publication Data
US 2022/0058801 A1    Feb. 24, 2022

Related U.S. Application Data

(60) Provisional application No. 62/780,663, filed on Dec. 17, 2018.

(51) Int. Cl.
*G06N 3/08* (2023.01)
*A61B 10/00* (2006.01)
(Continued)

(52) U.S. Cl.
CPC ........... *G06N 3/08* (2013.01); *A61B 10/0041* (2013.01); *G06F 18/24323* (2023.01);
(Continued)

(58) Field of Classification Search
CPC ............ G06N 3/08; G06N 3/045; G06N 5/01; G06N 20/10; G06N 20/20; A61B 10/0041;
(Continued)

(56) References Cited

U.S. PATENT DOCUMENTS

2016/0078634 A1    3/2016  Wang et al.

FOREIGN PATENT DOCUMENTS

WO    WO2010088688    8/2010
WO    WO2015113895    8/2015

OTHER PUBLICATIONS

Vandenberghe, M.E., Scott, M.L., Scorer, P.W., Söderberg, M., Balcerzak, D. and Barker, C., 2017. Relevance of deep learning to facilitate the diagnosis of HER2 status in breast cancer. Scientific reports, 7(1), p. 45938.*

(Continued)

*Primary Examiner* — Zhitong Chen
(74) *Attorney, Agent, or Firm* — Smith Gambrell & Russell LLP

(57) ABSTRACT

Embodiments of the present systems and methods may provide improved capability to predict the risk of recurrence of ductal carcinoma in situ (DCIS) conditions using whole slide image analysis based on machine learning techniques. For example, in an embodiment, a computer-implemented method for determining treatment of a patient may comprise receiving an image of living tissue of a patient, annotating the entire image into tissue structures, extracting texture features from the annotated image, determining a distribution of the extracted texture features relative to tissue conditions, classifying the patient into a risk group based on (Continued)

the distribution, and treating the patient accordingly based on the risk group.

24 Claims, 23 Drawing Sheets

(51) Int. Cl.
G06F 18/243 (2023.01)
G06T 7/00 (2017.01)
G06T 7/40 (2017.01)
G06V 10/20 (2022.01)
G06V 10/26 (2022.01)
G06V 10/40 (2022.01)
G16H 30/40 (2018.01)
G16H 50/20 (2018.01)
G16H 50/30 (2018.01)

(52) U.S. Cl.
CPC .............. *G06T 7/0012* (2013.01); *G06T 7/40* (2013.01); *G06V 10/20* (2022.01); *G06V 10/26* (2022.01); *G06V 10/40* (2022.01); *G16H 30/40* (2018.01); *G16H 50/20* (2018.01); *G16H 50/30* (2018.01); *G06T 2207/20084* (2013.01); *G06T 2207/30024* (2013.01); *G06T 2207/30068* (2013.01); *G06V 2201/03* (2022.01)

(58) Field of Classification Search
CPC . G06F 18/24323; G06F 18/00; G06T 7/0012; G06T 7/40; G06T 2207/20084; G06T 2207/30024; G06T 2207/30068; G06V 10/20; G06V 10/26; G06V 10/40; G06V 2201/03; G16H 30/40; G16H 50/20; G16H 50/30; Y02A 90/10
See application file for complete search history.

(56) References Cited

OTHER PUBLICATIONS

Irshad, H., Veillard, A., Roux, L. and Racoceanu, D., 2013. Methods for nuclei detection, segmentation, and classification in digital histopathology: a review-current status and future potential. IEEE reviews in biomedical engineering, 7, pp. 97-114.*

Hou, L., Samaras, D., Kurc, T.M., Gao, Y., Davis, J.E. and Saltz, J.H., 2016. Patch-based convolutional neural network for whole slide tissue image classification. In Proceedings of the IEEE conference on computer vision and pattern recognition (pp. 2424-2433).*

Bejnordi, B.E., Zuidhof, G., Balkenhol, M., Hermsen, M., Bult, P., van Ginneken, B., Karssemeijer, N., Litjens, G. and van der Laak, J., 2017. Context-aware stacked convolutional neural networks for classification of breast carcinomas in whole-slide histopathology images. Journal of Medical Imaging, 4(4), pp. 04450.*

Hamilton, P.W., Bartels, P.H., Thompson, D., Anderson, N.H., Montironi, R. and Sloan, J.M., 1997. Automated location of dysplastic fields in colorectal histology using image texture analysis. The Journal of Pathology: A Journal of the Pathological Society of Great Britain and Ireland, 182(1), pp. 68-75 (Hamilton).*

International Search Report and Written Opinion of the International Searching Authority in International Application No. PCT/US2019/066629 dated Mar. 3, 2020; 11 pages.

Rulaningtyas, et al., "Histopathology Grading Identification of Breast Cancer Based on Texture Classification Using GLCM and Neural Network Method," Journal of Physics, Conference Series, vol. 1120, Conference 1, Sep. 20-21, 2018; 10 pages.

* cited by examiner

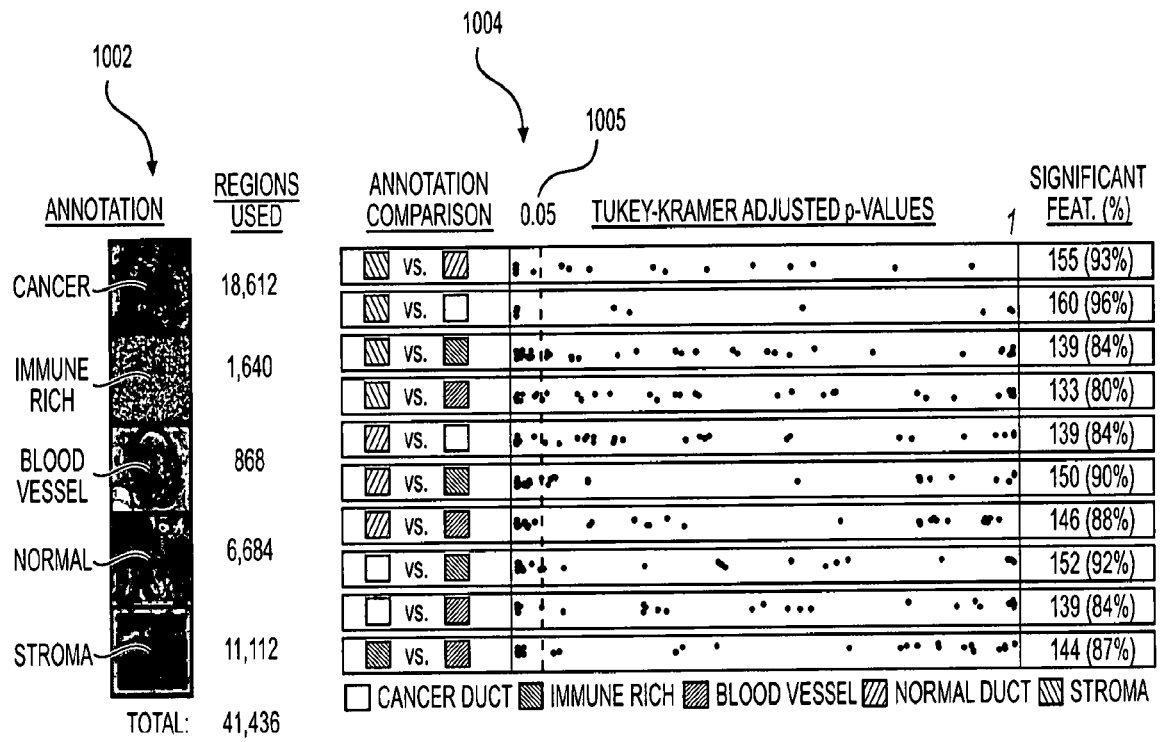
FIG. 10A
FIG. 10B
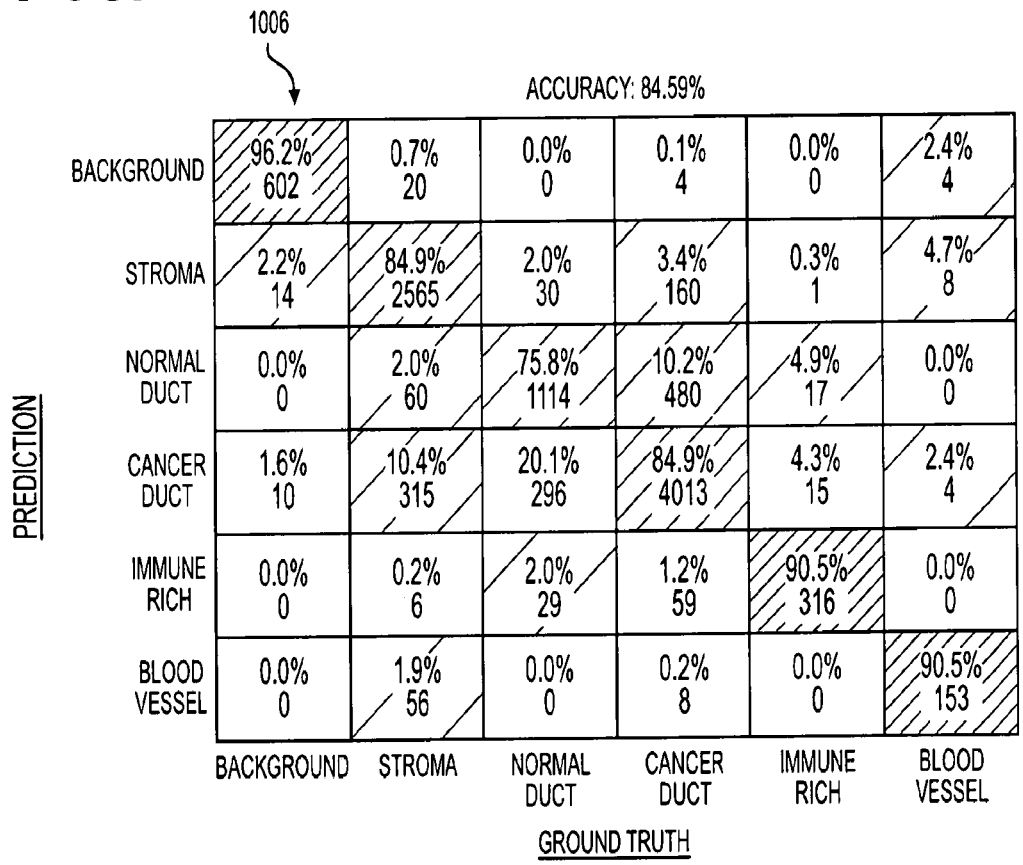
FIG. 10C

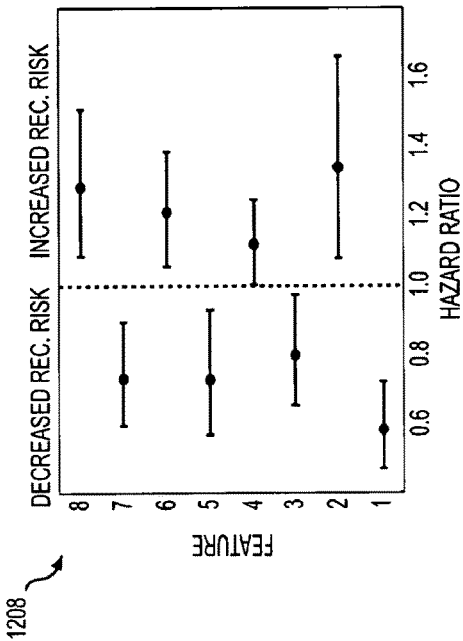
FIG. 12B
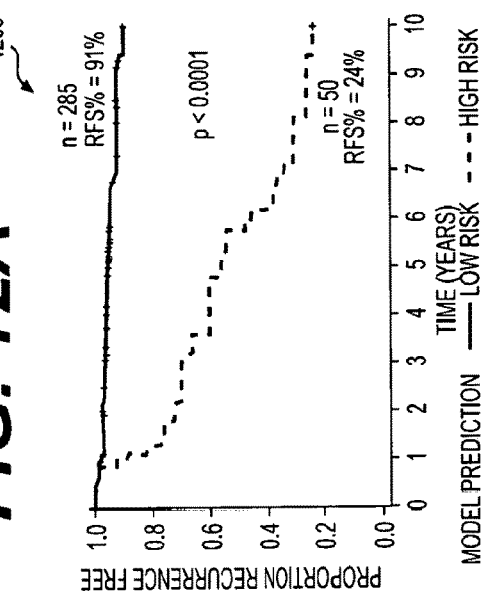
FIG. 12D
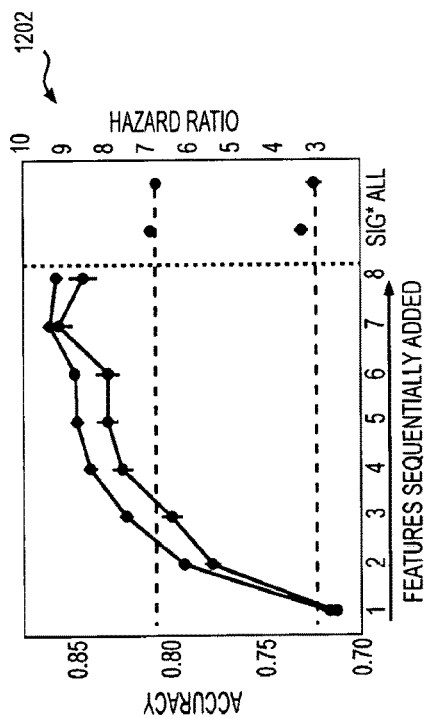
FIG. 12A
FIG. 12C

| TRAINING COHORT COX REGRESSION | | | | | | | |
|---|---|---|---|---|---|---|---|
| VARIABLES | | UNIVARIATE ANALYSIS | | | MULTIVARIATE ANALYSIS | | |
| | | HAZARD RATIO | 95% CONFIDENCE INTERVAL | P-VALUE | HAZARD RATIO | 95% CONFIDENCE INTERVAL | P-VALUE |
| RECURRENCE FREE SURVIVAL | | | | | | | |
| PREDICTIVE MODEL | LOW RISK VS. HIGH | 11.617 | 5.334 - 25.303 | <0.0001 | 12.542 | 5.435 - 28.946 | <0.0001 |
| COMEDO NECROSIS | ABSENT VS. PRESENT | 0.839 | 0.411 - 1.713 | 0.6302 | 0.651 | 0.255 - 1.661 | 0.3689 |
| SIZE | PER mm | 0.979 | 0.957 - 1.003 | 0.0812 | 0.982 | 0.958 - 1.007 | 0.1533 |
| GRADE | 1 AND 2 VS. 3 | 1.252 | 0.560 - 2.801 | 0.5836 | 1.305 | 0.452 - 3.771 | 0.6223 |
| MARGIN | NEGATIVE VS. POSITIVE | 1.226 | 0.167 - 8.994 | 0.8412 | 0.617 | 0.075 - 5.071 | 0.6536 |
| AGE | PER YEAR | 0.981 | 0.942 - 1.022 | 0.3669 | 1.007 | 0.965 - 1.052 | 0.7385 |
| RADIOTHERAPY | YES VS. NO | 1.073 | 0.479 - 2.403 | 0.8636 | 1.113 | 0.439 - 2.818 | 0.8219 |

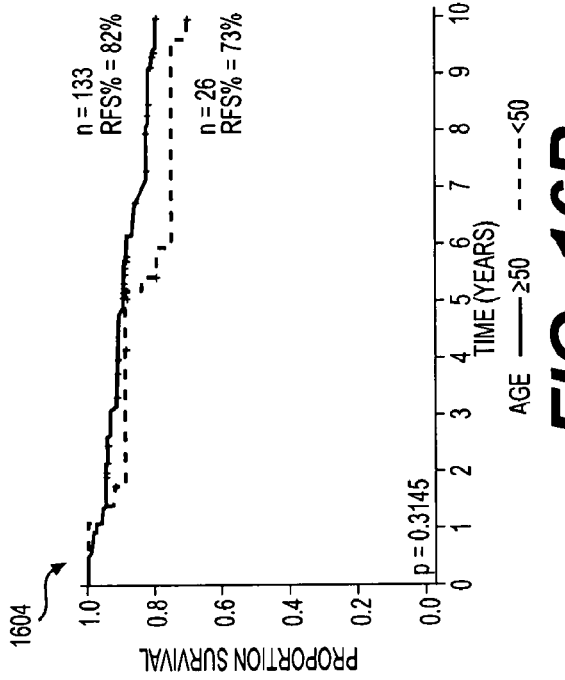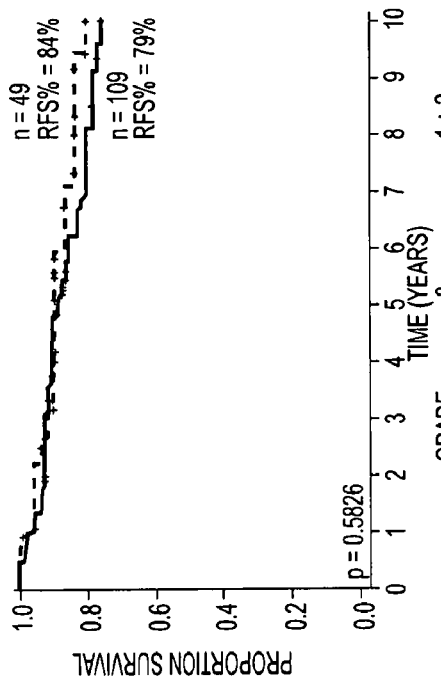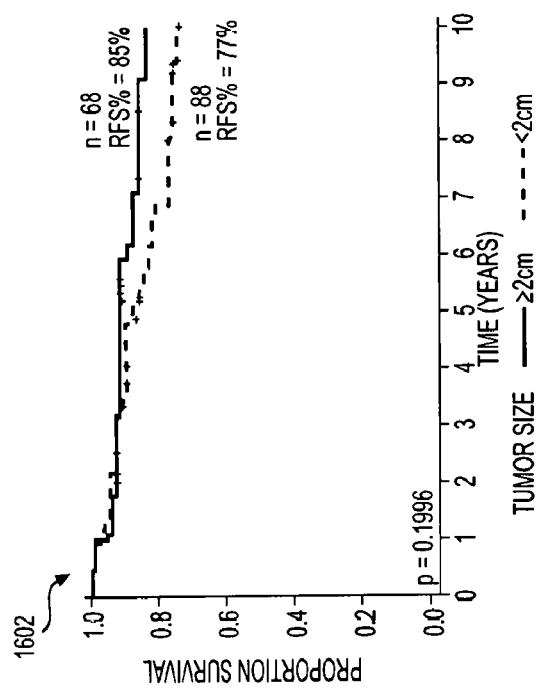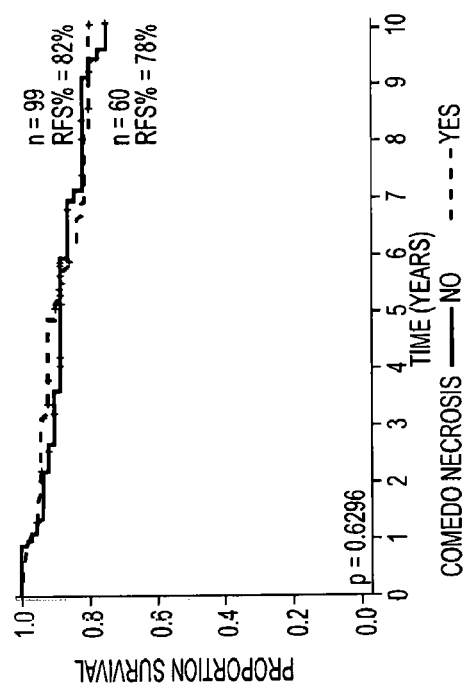

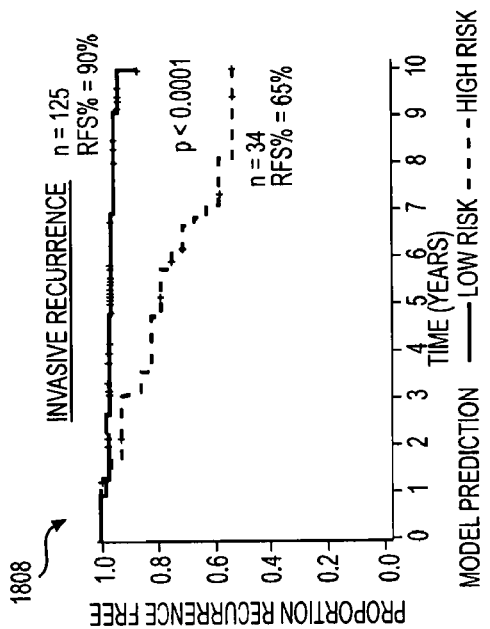
FIG. 18B
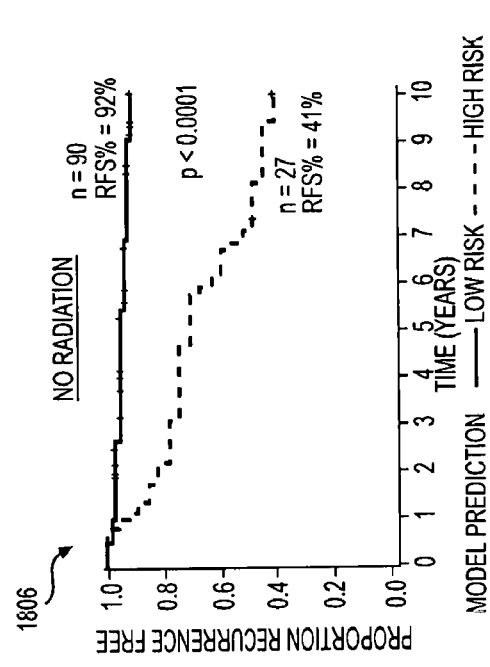
FIG. 18D
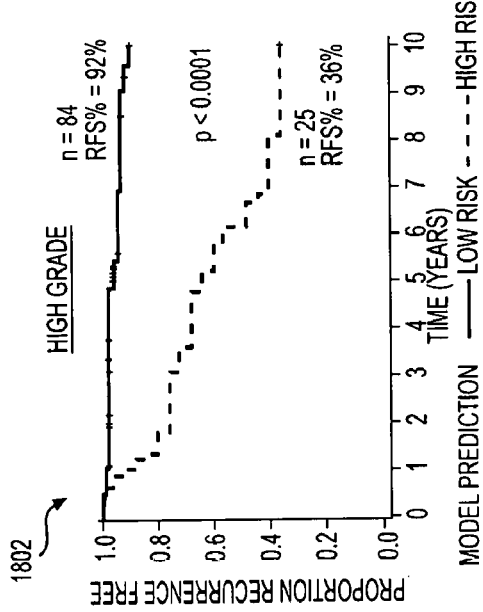
FIG. 18A
FIG. 18C

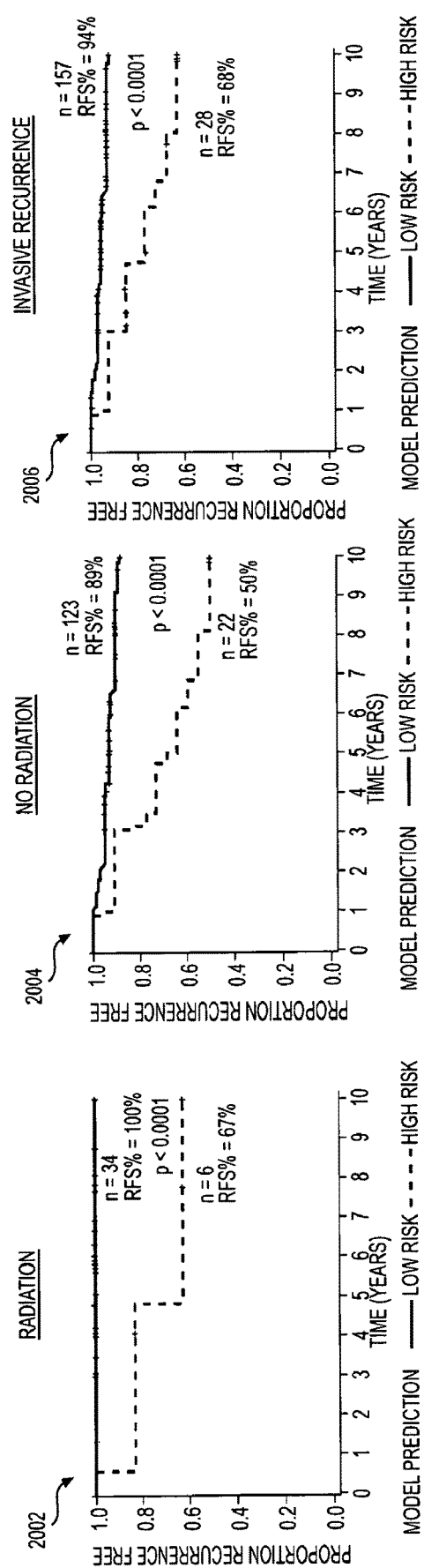

| TRAINING COHORT COX REGRESSION | | | | | | | |
|---|---|---|---|---|---|---|---|
| VARIABLES | | UNIVARIATE ANALYSIS | | | MULTIVARIATE ANALYSIS | | |
| | | HAZARD RATIO | 95% CONFIDENCE INTERVAL | P-VALUE | HAZARD RATIO | 95% CONFIDENCE INTERVAL | P-VALUE |
| RECURRENCE FREE SURVIVAL | | | | | | | |
| PREDICTIVE MODEL | LOW RISK VS. HIGH | 6.39 | 2.961 - 13.789 | <0.0001 | 6.752 | 3.066 - 14.865 | <0.0001 |
| COMEDO NECROSIS | ABSENT VS. PRESENT | 0.805 | 0.323 - 2.006 | 0.6417 | 1.087 | 0.423 - 2.798 | 0.862 |
| SIZE | PER mm | 1.003 | 0.986 - 1.021 | 0.7131 | 1.008 | 0.990 - 1.026 | 0.3941 |
| MARGIN | NEGATIVE VS. POSITIVE | - | - | 0.9984 | - | - | 0.9918 |
| AGE | PER YEAR | 1.031 | 0.979 - 1.085 | 0.2472 | 1.034 | 0.981 - 1.089 | 0.2106 |
| RADIOTHERAPY | YES VS. NO | 0.372 | 0.088 - 1.579 | 0.18 | 0.397 | 0.091 - 1.733 | 0.2192 |

PREDICTING DCIS RECURRENCE RISK USING A MACHINE LEARNING-BASED HIGH-CONTENT IMAGE ANALYSIS APPROACH

CROSS-REFERENCE TO RELATED APPLICATIONS

This application claims the benefit of U.S. Provisional Application No. 62/780,663, filed Dec. 17, 2018, the contents of which are incorporated herein in their entirety.

BACKGROUND

The present invention relates to techniques that provide improved capability to predict the risk of recurrence of DCIS conditions using whole slide image analysis based on machine learning techniques.

Around 20% of screen-detected breast cancers are preinvasive ductal carcinoma in situ (DCIS). The overall risk from DCIS stems almost exclusively from local recurrence. However, there are increasing concerns of over-treating DCIS, particularly in the screening settings. Current clinicopathological markers are insufficient to accurately predict outcome and guide further treatment for each patient. As a result, with current techniques, there is significant risk that patients may be over-treated or under-treated.

Accordingly, a need arises for techniques that provide improved capability to predict the risk of recurrence of DCIS conditions, as well as to provide more personalized therapy and reduce the risk of over-treatment or under-treatment.

SUMMARY

Embodiments of the present systems and methods may provide improved capability to predict the risk of recurrence of ductal carcinoma in situ (DCIS) conditions using whole slide image analysis based on machine learning techniques. Embodiments may use a plurality of hematoxylin texture features, from varied tissue architecture, to build a machine learning model to predict the 10-year risk of recurrence. For example, in a test (HR=12.6 n=335, p<0.0001) and validation (HR=6.39 n=185, p<0.0001), embodiments of the present systems and methods were applied to cohorts from Nottingham University Hospitals. Embodiments of the present systems and methods may outperform common clinicopathological variables in predicting DCIS recurrence (p<0.0001). Taken together, embodiments may clearly stratify patients to different treatment groups, such as those requiring adjuvant radiation (validation cohort: HR=5.5 n=145, p<0.0001)

For example, in an embodiment, a computer-implemented method for determining treatment of a patient may comprise receiving an image of living tissue of a patient, annotating the entire image into tissue structures, extracting texture features from the annotated image, determining a distribution of the extracted texture features relative to tissue conditions, classifying the patient into a risk group based on the distribution, and treating the patient accordingly based on the risk group.

In embodiments, the annotating may comprise preprocessing the image using color normalization and downsampling, extracting a plurality of patches from the preprocessed image using a sliding window, color deconvoluting each of the plurality of patches to a hematoxylin layer, extracting a plurality of texture features from the plurality of patches, inputting the extracted texture features into a random forest to output a probability of each patch belonging to a category of tissue structure, and combining the patch probabilities to form an image annotation of tissue structures. The plurality of texture features may comprise at least one selected texture feature, at least one convolutional neural network fully connected terminal layer features, or a combination of the two. The determining the distribution may comprise determining feature distributions, spatial features which compare distances between different tissue regions, and region confidence. The classifying may comprise selecting a plurality of features and inputting the selected features into a random forest to output a probability of a condition to be treated and a treatment recommendation. The living tissue is breast tissue and the risk groups relate to risk of recurrence of breast cancer. The breast cancer is ductal carcinoma in situ. The categories of tissue structure may comprise malignant duct, immune rich stroma, non-immune rich stroma, non-cancerous duct, and blood vessel.

In an embodiment, a system for detecting malicious email messages, the system may comprise a processor, memory accessible by the processor, and computer program instructions stored in the memory and executable by the processor to perform receiving an image of living tissue of a patient, the image comprising a stained histopathology slide, annotating the entire image into tissue structures, extracting texture features from the annotated image, determining a distribution of the extracted texture features relative to tissue conditions, classifying the patient into a risk group based on the distribution, and treating the patient accordingly based on the risk group.

In an embodiment, a computer program product for detecting malicious email messages, the computer program product may comprise a non-transitory computer readable storage having program instructions embodied therewith, the program instructions executable by a computer, to cause the computer to perform a method that may comprise receiving an image of living tissue of a patient, the image comprising a stained histopathology slide, annotating the entire image into tissue structures, extracting texture features from the annotated image, determining a distribution of the extracted texture features relative to tissue conditions, classifying the patient into a risk group based on the distribution, and treating the patient accordingly based on the risk group.

BRIEF DESCRIPTION OF THE DRAWINGS

The details of the present invention, both as to its structure and operation, can best be understood by referring to the accompanying drawings, in which like reference numbers and designations refer to like elements.

FIG. 10 illustrates an example of annotation results of the process shown in FIG. 1.

FIG. 12 illustrates an example of full slide results of full slide feature selection shown in FIG. 2.

FIG. 16 illustrates an example of stratification of patients in the training cohort using standard clinical variables.

FIG. 18 illustrates an example of cross validated Kaplan-Meier curves of patients within the training cohort.

FIG. 20 illustrates an example of cross validated Kaplan-Meier curves of patients within the validation cohort.

DETAILED DESCRIPTION

Figure 1:
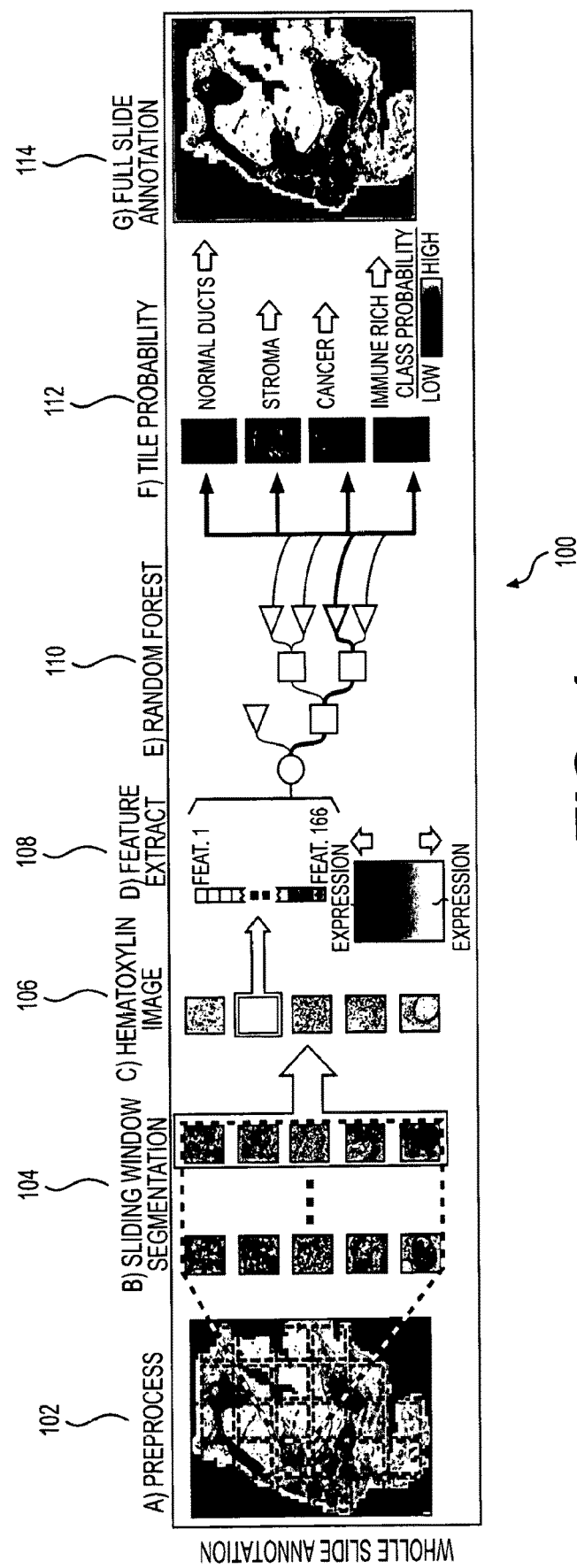
FIG. 1 is an exemplary flow diagram of a first portion of a process in accordance with embodiments of the present techniques.

Embodiments of the present systems and methods may provide improved capability to predict the risk of recurrence of ductal carcinoma in situ (DCIS) or other solid tumors such as, but not limited to, pancreatic, liver, lung, brain, and prostate cancers using whole slide image analysis based on machine learning techniques. Embodiments may use a plurality of texture features obtained from either hematoxylin and eosin stained tissue or via a plurality of different immunohistochemical stains, from varied tissue architecture, to build a machine learning model to predict the 10-year risk of recurrence. For example, in a test (HR=12.6 n=335, p<0.0001) and validation (HR=6.39 n=185, p<0.0001), embodiments of the present systems and methods were applied to cohorts from Nottingham University Hospitals. Embodiments of the present systems and methods may outperform common clinicopathological variables in predicting DCIS recurrence (p<0.0001). Taken together, embodiments may clearly stratify patients to different treatment groups, such as those requiring adjuvant radiation (validation cohort: HR=5.5 n=145, p<0.0001)

The incidence of ductal carcinoma in situ (DCIS) has risen rapidly over the past few decades, affecting approximately one in every four women diagnosed with breast cancer within the United States and estimated to affect over 1 million US women by 2020. DCIS is the non-obligate penultimate pre-invasive form of invasive breast cancer, where malignant cells are confined to the lumen of a mammary duct by an intact outer myoepithelial layer and basement membrane. Despite the similarity at the genetic profile, risk factors, morphology and even the degree of heterogeneity to their invasive counterpart, untreated DCIS progresses into invasive conditions only in ~40% of cases, some only after 4 decades, lowered to ~10-20% after treatment. Nonetheless, patients are often treated aggressively, as the mechanism of progression has not been elucidated. Despite the excellent overall survival rate of DCIS, patients in routine practice are often over-treated. This typically stems from the inability to identify those tumors which are likely to recur with an acceptable degree of confidence.

A major goal for treating DCIS is to curb local relapse. Common histopathology factors such as age of diagnosis, DCIS growth pattern, tumor size, margin status, nuclear grade, presence of comedo necrosis, and combinations of the aforementioned factors (such as in the Van Nuys prognostic index or prognostic Nomograms) have been shown to have some limited value in predicting recurrence. However, there is still uncertainty as to what constitutes a high risk DCIS. Thus, there is still a critical need for novel biomarkers that can improve recurrence risk stratification for DCIS patients.

With the advent of technology able to process high throughput data, computational pathology has shown promise in medical prognosis. By integrating image analysis, data generation, and medical statistics, computational pathology enables quantitative tissue analysis. Although relatively new, computational pathology has already shown marked success, especially with hematoxylin and eosin stained (H&E) tumor tissues. Multiple cancer types including invasive breast carcinoma, prostate, colon, and lung have benefited using these techniques to assist with diagnosis, tissue classification/segmentation, or patient prognosis. Whole slide quantitative image analysis pipelines have shown to have significant discriminatory success not only using features stemming from pixel (stain) intensities, but morphometric features and texture. Within DCIS, various scales of these image features have been studied using H&E tissue. One of the earliest utilizations for duct analysis was quantifying image features of comedo necrosis to predict recurrence. At the cellular level, chromatin distribution, long considered a computationally quantifiable feature of cancer cells, has been used to predict DCIS recurrence and shown to outperform its pathological analogue; nuclear grade. However, these results focus on very specific characteristics of the DCIS and miss out on the extraordinary surrounding information.

Human limitations (due to factors such as limited time, visual discriminatory ability, and lack of human concordance) also exist within the pathological grading of DCIS. Notably, the breadth of DCIS grading is limited to a single (high grade) duct, and that oftentimes histopathologic features are grouped into distinguishable categories. This simplification of analysis discounts a) the prognostic value of surrounding microenvironment which could have biological relevance such as with fibroblasts, immune cells, blood vessels, and even alterations in non-cancerous epithelial cells and b) the tremendous heterogeneity within DCIS, which cannot be categorized in a fundamentally meaningful way. Quantitatively analyzing the whole slide, dubbed whole slide image analysis (WSI) could potentially mitigate these limitations. While WSI has been used to detect and segment DCIS lesions, its potential in analyzing the surrounding environment alongside the image features of cancerous ducts to establish a DCIS recurrence risk, is unknown.

Figure 2:
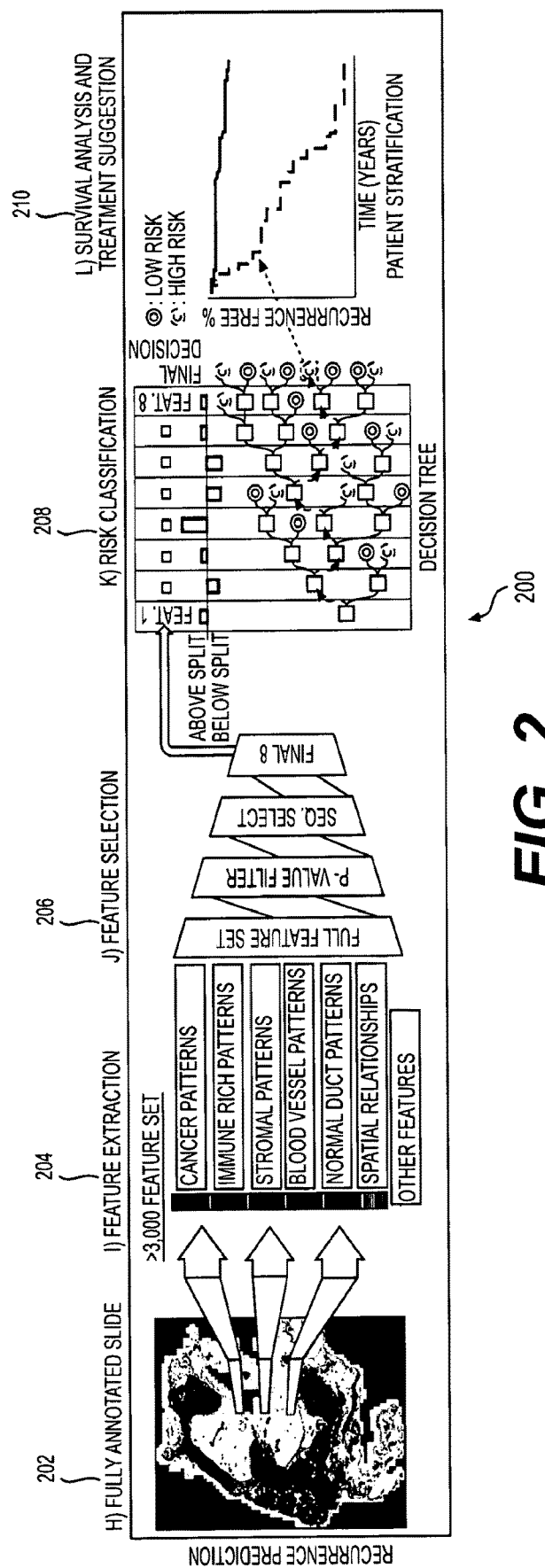
FIG. 2 is an exemplary flow diagram of a second portion of a process in accordance with embodiments of the present techniques.

Embodiments of the present systems and methods may be used to identify features obtained from the texture of H&E slides, and may include a novel two-step classification approach to predict 10 year recurrence rates in patients treated with breast conservative surgery (BCS). A flow diagram of a first portion 100 of a process in accordance with embodiments of the present techniques is shown in FIG. 1. In portion 100, the whole slide may be annotated into prognostic structures such as malignant ducts of DCIS, surrounding breast parenchyma/ducts, blood vessels, and stromal regions with and without obvious immune cell infiltration. A flow diagram of a second portion 200 of a process in accordance with embodiments of the present techniques is shown in FIG. 2. The portion 200 may use the fully annotated slide images for feature extraction, which includes quantifying the distribution of the texture features within each annotation and spatial relationships relative to tissue conditions. These final features may then be used together to classify patients into distinct groups that showed a strong association with DCIS recurrence rate (risk group).

In portion 100, shown in FIG. 1, an image slide may be preprocessed 102 through whole slide color normalization and down-sampling. At 104, a sliding window may extract patches of the preprocessed slide. At 106, the patches may be color deconvoluted to a hematoxylin layer. At 108, values for features, for example, a plurality of texture features may be extracted from the patches. At 110, the extracted features may be input into a random forest, which may output 112 a probability of each patch belonging to a specific category (malignant duct, immune rich stroma, non-immune rich stroma, non-cancerous duct, and blood vessel). At 114, the patch probabilities may be combined to produce a whole slide annotation 114. Turning to FIG. 2, for recurrence prediction, each annotation 202 may be analyzed 204 through feature distributions, spatial features which compare distances between different classes, and other features such as region confidence. At 206, a final feature list may be selected. At 208, the final feature list may be to train 208 a machine learning classifier, such as a random forest classifier, to predict 210 high- versus low-risk of recurrence and to provide a recommendation of additional therapy.

Methodology. An exemplary study was conducted to test the effectiveness of the present systems and methods. The study utilized particular examples of hardware and software, as well as particular examples of parameter selection. However, it is to be noted that these items are merely examples. The present systems and methods are not limited to the particular examples of hardware and software described herein, nor are they limited to the particular examples of parameter selection. The exemplary study is described below, with reference to FIGS. 1 and 2.

Study population. In the exemplary study that was conducted, the study population was obtained from patients presenting at Nottingham City Hospital DCIS series, spanning the period from 1989 to 2012. One hundred and fifty nine patients were used for the model development and training and a further 185 were used for validation. Patients used in this study were restricted to pure DCIS cases treated with breast conserving surgery (BCS), rather than mastectomy. The DCIS classification was initially identified through different pathology data storage systems and further verified through slides review by a medical professional, such as, a pathologist. Cases with definite stromal invasion were excluded regardless of the size of invasive foci. Details on clinicopathological and demographic information, and follow-up data were obtained. Recurrence free survival (RFS) was calculated from the date of diagnosis until the first ipsilateral breast local recurrence. Cases with contralateral recurrences were censored at the time of recurrence.

Tumor Slide Selection. An example of tumor slide selection is as follows: A representative formalin-fixed paraffin-embedded (FFPE) tumor block (donor) for each patient's specimen was retrieved. Blocks containing viable tumor tissue were chosen. A fresh full-face section of 4 micrometers (µm) thickness was cut from each block, stained with H&E, and reviewed. Slide scanning was performed with a high-resolution slide scanner (PANNORAMIC® 250 FLASH III®, 3DHISTECH®) Automatic scanner mode was selected with OPTOVAR® position Pos10_1.6_1 (PANNORAMIC® 250 FLASH III®, 3DHISTECH®) for good quality images scanning option (JPEG: 80, 8 bit). Flash mode was selected with 6 focus distance in field of view single layer using stitching mode without Bright-field compensation.

Figure 3:
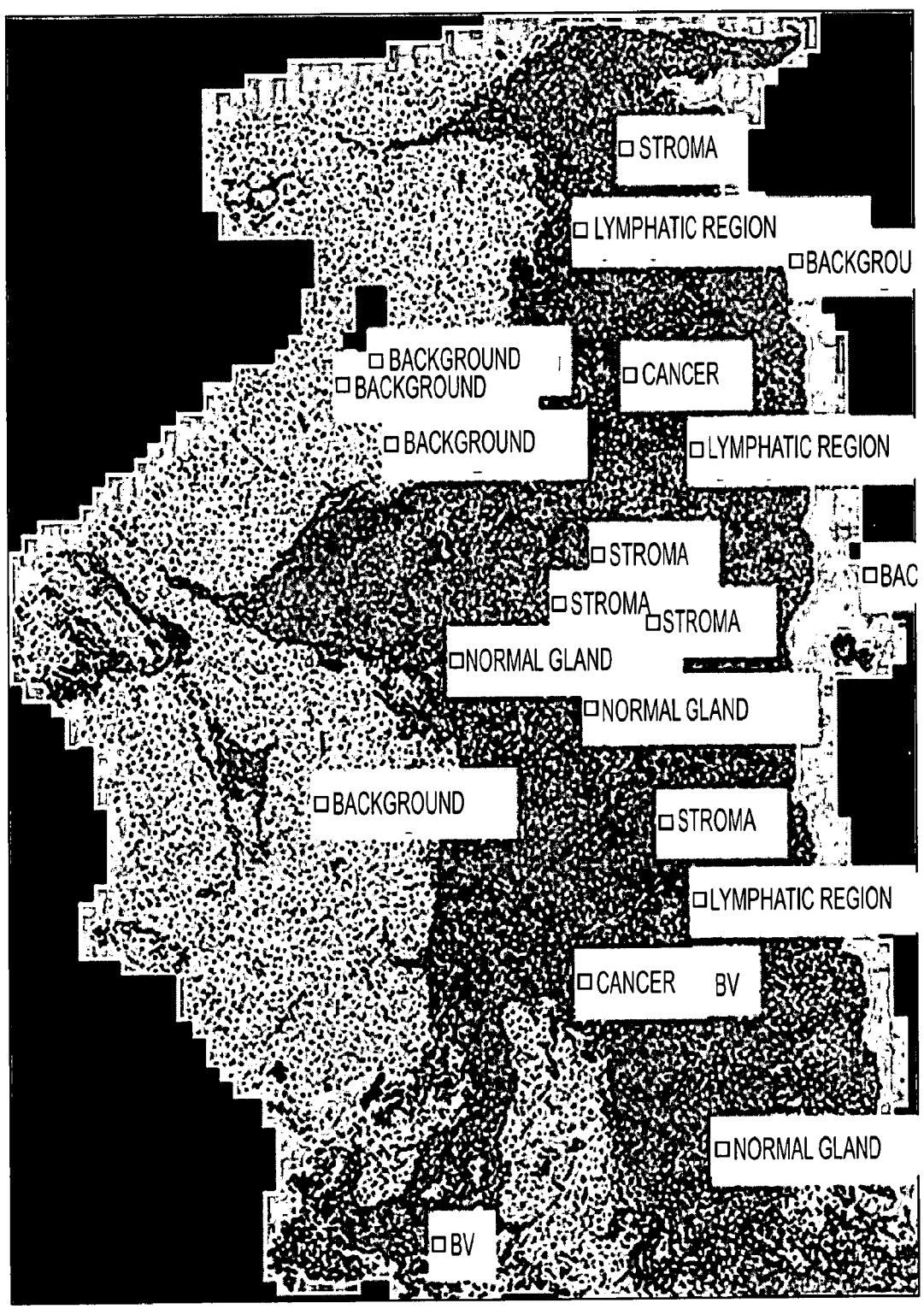
FIG. 3 illustrates an example of a Graphical User Interface (GUI) developed to allow for ground truth annotations used for classifier training.

Automated Full Slide Annotation. For example, Open-Slide software may be used for the 4× down-sampling of the full slides for computational feasibility. An example of a Graphical User Interface (GUI) 300 developed to allow for ground truth annotations used for classifier training is shown in FIG. 3. Through this interface, a user may select regions representative of each class, from which the program will apply feature extraction from multiple 50×50 pixel ground truth windows 104 for training the classifier to identify stroma, adjacent nonmalignant epithelial ducts, cancerous ducts, stromal regions with large immune (lymphocyte) infiltration, and blood vessels. This GUI permitted accumulation of accurate training samples from multiple slides in a short time. Each 50×50 pixel window, used, was color normalized to a standard H&E staining distribution, to account for specimen and staining variability, and improve classification performance.

The normalized windows are then color deconvoluted 106 into separate hematoxylin and eosin channels through an optical density matrix which contains the relative absorbance of each stain in the RGB color channel, as shown, for example, in Table 1. This matrix may be used to deconvolute RGB H&E images into greyscales of each layer whose intensity correlated with stain absorbance.

TABLE 1

| R | G | B | |
|---|---|---|---|
| 0.644 | 0.717 | 0.267 | Hematoxylin |
| 0.093 | 0.954 | 0.283 | Eosin |
| 0.636 | 0.001 | 0.772 | Zero Matrix |

Texture features, an exemplary breakdown of which is shown in Table 2, are extracted 108 from the deconvoluted hematoxylin channel for the random forest classifier training.

TABLE 2

| Textural Feature Type | No. of Features | Source |
|---|---|---|
| Entropy | 1 | (3) |
| Gray-Level Co-occurrence Matrix (GLCO) | 16 | (4) |
| Gray-Level Run Length (GRLRL) | 44 | (5, 6) |

TABLE 2-continued

| Textural Feature Type | No. of Features | Source |
|---|---|---|
| Segmentation-based Fractal Texture Analysis (STFA) | 45 | (7, 8) |
| Gabor wavelet filters | 60 | (9-12) |
| Sum: | 166 | |

Figure 23:
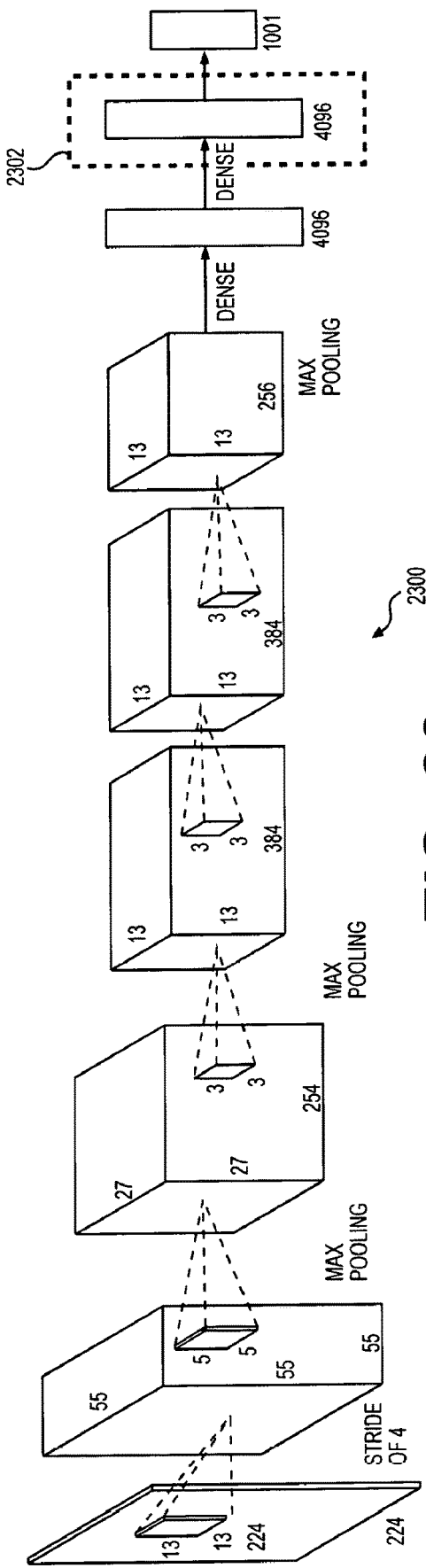
FIG. 23 illustrates an example of a trained Convolutional neural network (CNN) from which useful features may be derived from, for example, the final fully connected layer.

The texture features shown in Table 2 are merely examples of suitable texture features that have been selected. Such features may be considered static and interpretable. In addition, Deep Learning features may be utilized. For example, useful features may be derived from the final fully connected layer of a trained Convolutional neural network (CNN). An example of such a layer 2302 in a trained network 2300 is shown in FIG. 23. Such CNN features are typically less interpretable than selected texture features as they typically have a large number of 'weights' which tune them. They may be trained and may produce different results for different trained problems. Such CNN features may be extracted and used as independent feature sets. For example, features from a CNN trained on one dataset may be used as training input for other classification methods, such as Random Forest and SVM.

Figure 4:
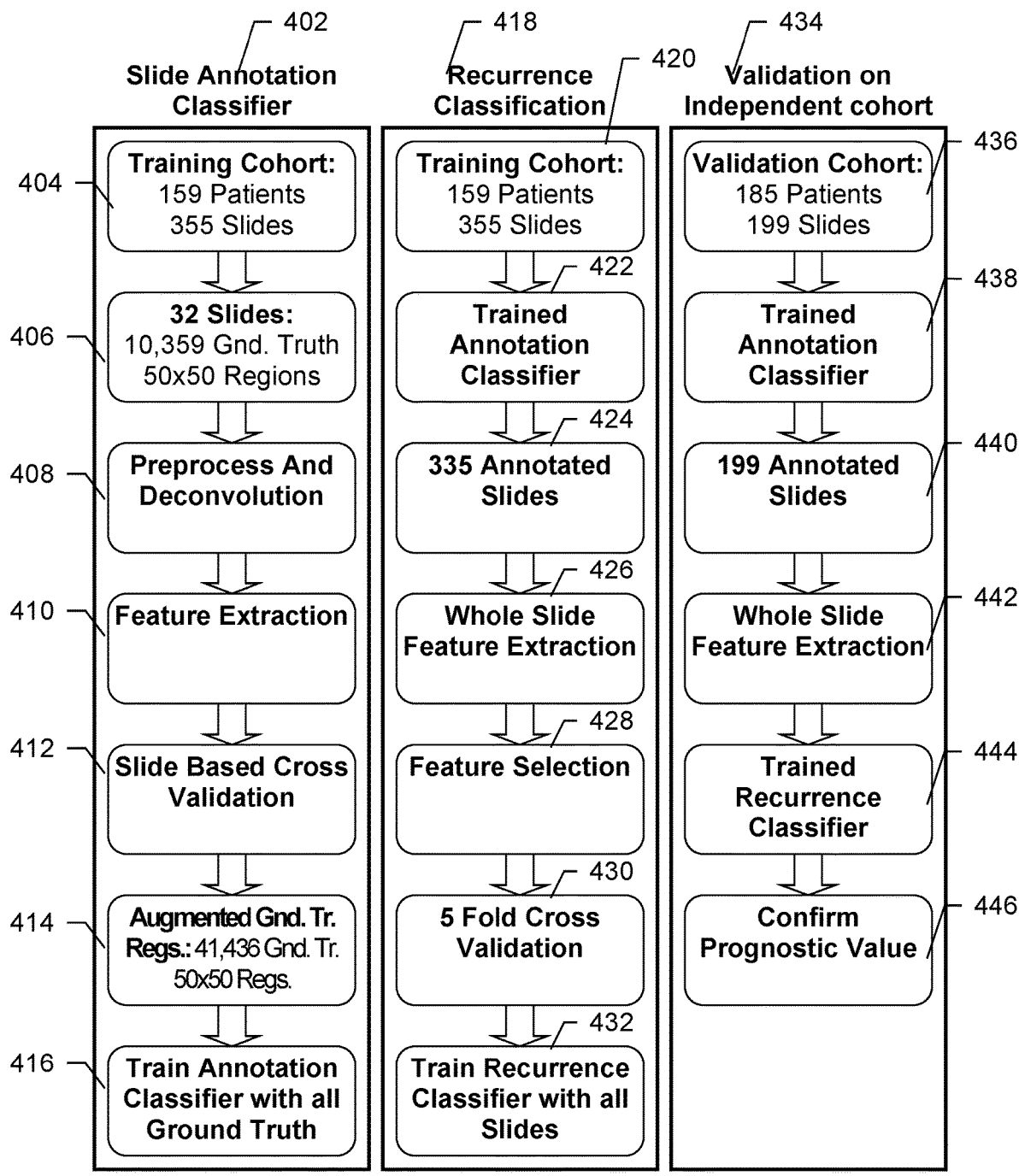
FIG. 4 is exemplary flow diagrams of slide annotation classifier development, recurrence classification, and validation on an independent cohort.

To reduce same slide bias, testing of the classification ability was performed on a slide-based leave-one-out cross-validation. Each held out set of windows used for testing was composed of (pathologist-annotated) ground truth regions from single individual slides, such that the test fold always consisted of extracted windows from a slide which was not used in training. To account for the vast textural heterogeneity seen in histology slides, we augmented the training tiles by 4-fold, by performing diagonal flipping, 90° rotation, and the combination of the two, on all training tiles. Tissue features extracted from the augmented set of windows were used to train a random forest classifier 110 for tissue annotation on the slide class. An example of the slide annotation classifier development 402 is shown in FIG. 4. As shown in the example, the slide annotation classifier was developed using a random selection of slides 406 within the training cohort 404. The ground truth regions were preprocessed and color deconvoluted 408 so that texture features could be extracted 410 from the hematoxylin distributions. Five-fold cross validation 412 was performed to determine the model's classification ability after which the training set was augmented 414 through rotation and transposition of ground truth regions and input into the final annotation classifier 416. The output of this random forest was the probability 112 of the input window to belong to each class with the predicted annotation determined by the highest probability. Full slides being processed by the WSI pipeline (i.e., slides that were not previously used for training the annotation classifier) were annotated through a grid approach wherein adjacent 50×50 pixel windows (that made up the full slide) were processed, such as at 102, 104, 106 of FIG. 1, as previously detailed for the training data, their features input into the trained random forest, such as at 108, 110 of FIG. 1, and the classified windows stitched together 114, such as at 112, 114 of FIG. 1. Additional post processing was done for the further analysis of spatial features (see next section) through the use of neighborhood voting. In this approach classified regions were amended if the sum of all its direct neighbor's trees classifications resulted in a larger proportion for a different annotation.

Figure 5:
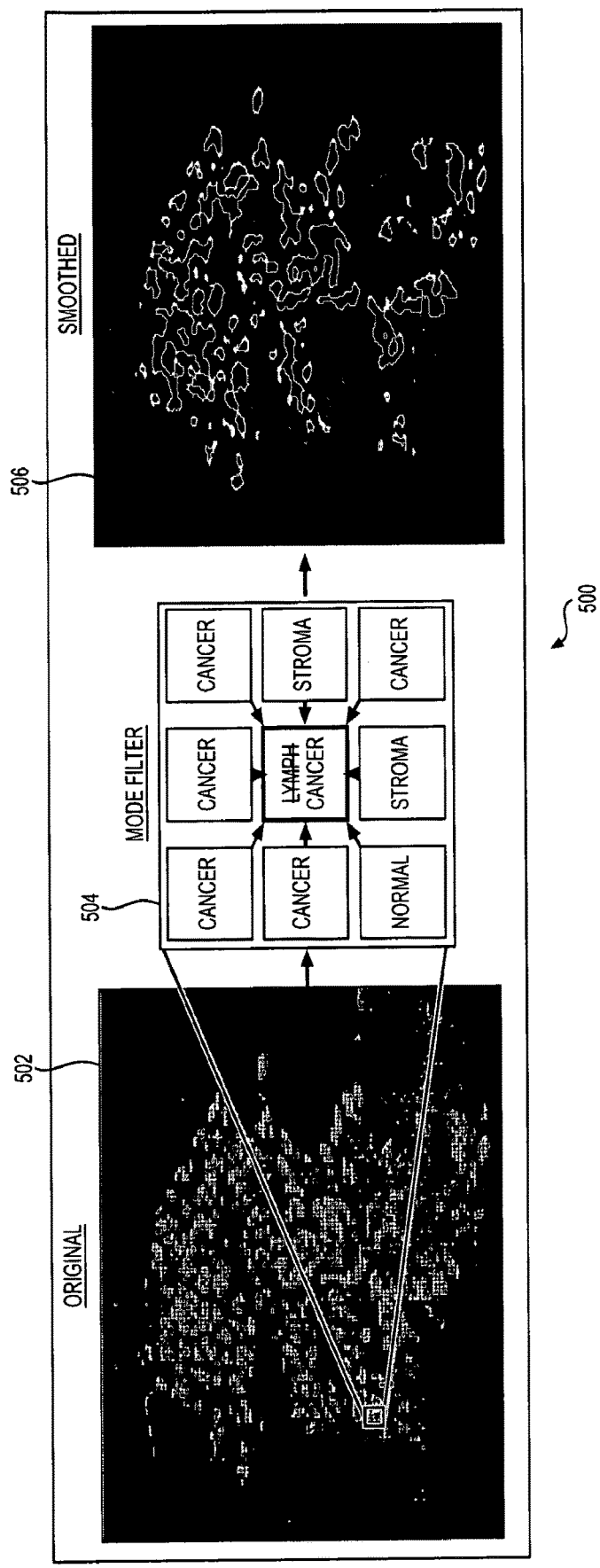
FIG. 5 illustrates an example of region smoothing using a mode (class appearing most often) filter.

FIG. 5 illustrates an example 500 of region smoothing using a mode (class appearing most often) filter 504. In this example, the middle tile was originally classified as a lymphocyte-dense region. The surrounding neighbors though, were predominantly classified as cancer; thus, the middle tile had its class changed to cancer. While this example shows the mode depending on each tile's predicted class, embodiments of the model may use the mode of tree predictions of surrounding neighbors to adjust the middle tile classification.

Full Slide Feature Optimization and Recurrence Prediction. Following automated slide annotation, a set of distinct full slide features can be extracted 202, for example as shown at 204 of FIG. 2. An example of features extracted from class-annotated virtual/digital slides is shown in Table 3.

TABLE 3

| Full-Slide Feature Type | No. of Features |
|---|---|
| Distribution Statistics | 3320 |
| Spatial Distance | 12 |
| Densities | |
| Class Proportions | 5 |
| Confidence Metric | 5 |

Figure 6:
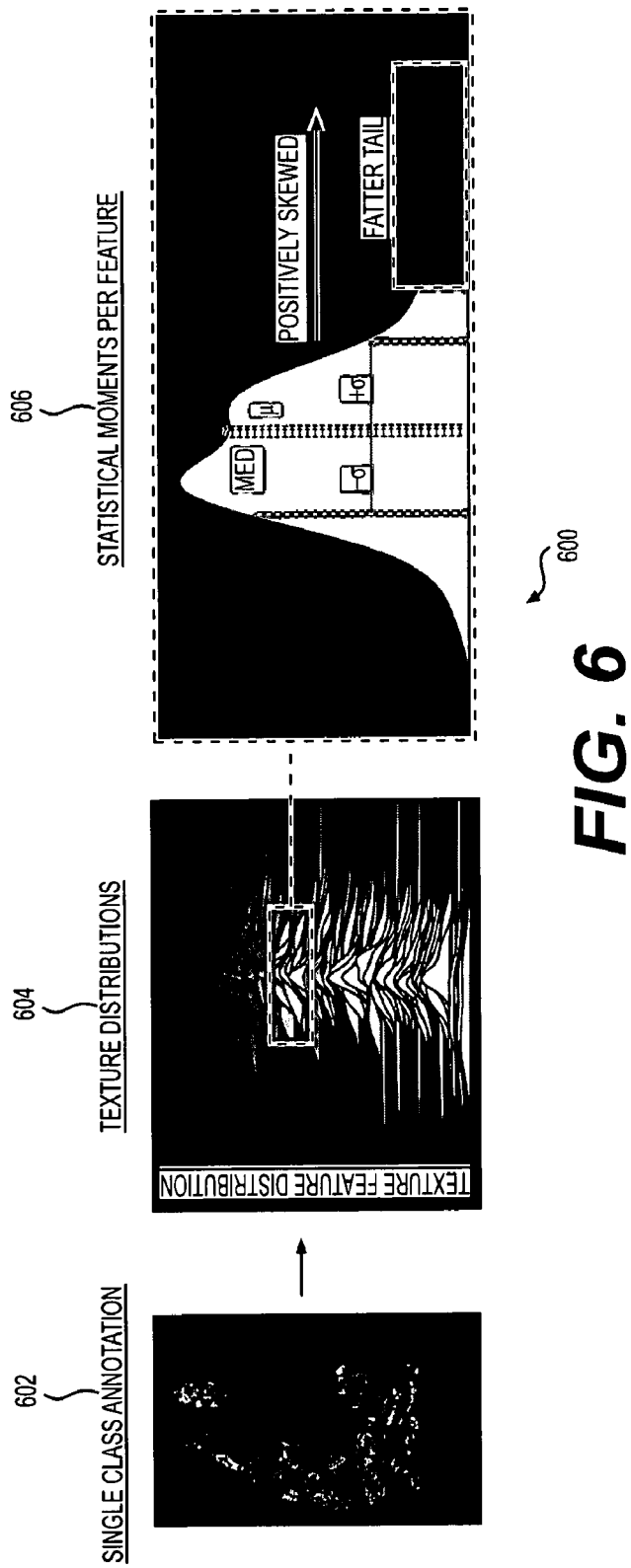
FIG. 6 illustrates an example of statistical moments obtained from full slide analysis.

In this example, the texture feature distribution statistics constitute the majority of evaluated features as they include the mean, standard deviation, skew, and kurtosis for each of the exemplary 166 textural features within each of the exemplary 5 annotated classes. The majority (99%) of these features consist of statistical moments of the exemplary 166 texture features for each annotated class and provide information on the shape of the texture features distribution for that class. An example 600 of the statistical moments obtained from full slide analysis is shown in FIG. 6. For each window for an annotated class 602 the distribution 604 of all texture features was computed. From each of these distributions, statistical moments 606, such as the mean, standard deviation, skew, and kurtosis were calculated and input as individual components of the full slide feature list. Additionally, spatial features were derived 204 that related the distance and size of cancer to either annotation blood vessels or lymphocyte rich regions, as literature points to both having spatial relevance, for example, according to Equation 1:

$$\text{Density Distance} = \frac{\sum_{i=1}^{n}\sum_{j=1}^{n}\frac{1}{D_{i,j}}*A_i*A_j}{\sum A_i} \quad (1)$$

Equation 1 shows an example of a Density Distance Statistic, which is a statistic comparing the size (A) and distance (D) between all (sum) cancer (i) areas (connected regions) and either immune-rich or blood vessel (BV) areas (j), normalized (divided) by the total cancer area.

Finally, proportions of each class, such as the amount of tumor on a slide (a quantity commonly calculated in cancer staging), and average annotation confidence (calculated by averaging the number of trees which voted for each annotated class, such that low values would be given if there was large ambiguity for any annotation on that slide) were included as features.

To reduce data dimensionality and improve training time and prediction accuracy, a feature reduction step was performed 206. First, we selected a maximum follow up time point past which a patient will be right censored and considered non-recurred. As patients who experience recurrence after a very long follow up may possess features resembling features in patients who do not recur, it becomes imperative to select a time point that is both clinically relevant and maximizes the number of significant features that separate recurring and non-recurring groups. Therefore, t-tests were run on all of the full slide features (texture distributions, spatial features, annotation proportions, and the confidence metric) between recurrence-free and recurring (at a specified time point) patients, starting at a follow-up period of 5 years, as most patients recur within 10 years of diagnosis. To identify the temporal change in significant features, the same process was performed for every additional year of follow-up until a maximum follow-up period of 25 years. The maximum follow-up time selected for our study was the one which provided the greatest number of significant features between patients who recurred by that time versus those that did not.

For the selected follow-up time, we filtered and sequentially selected the list of candidate features within multiple machine learning models to build an optimized classifier. The full features set was first filtered to those that were significantly different (t-test p-value <0.05) between slides of patients who recurred versus those that did not. The retained features were further evaluated by sequential forward feature selection with random forest, k-nearest neighbor, and support vector machine classifiers 206, with the goal of identifying a classifier and a subset of features that together best predict the DCIS risk recurrence. The retained features were sequentially added one by one to the training of a machine learning classifier 208, and the resulting classifier's performance was measured through the misclassification rate observed upon 5-fold cross validation. Examples of such classifiers may include a random forest classifier, a decision tree classifier, a support vector machine (SVM), K-nearest neighbors (KNN) etc. Features which minimized the misclassification rate the most were retained. The process of adding features was continued until there was no further improvement in classifier's performance. The selected features alongside the classifier which provided the best cross validated accuracy and HR was selected for the final DCIS recurrence risk prediction model.

Figure 7:
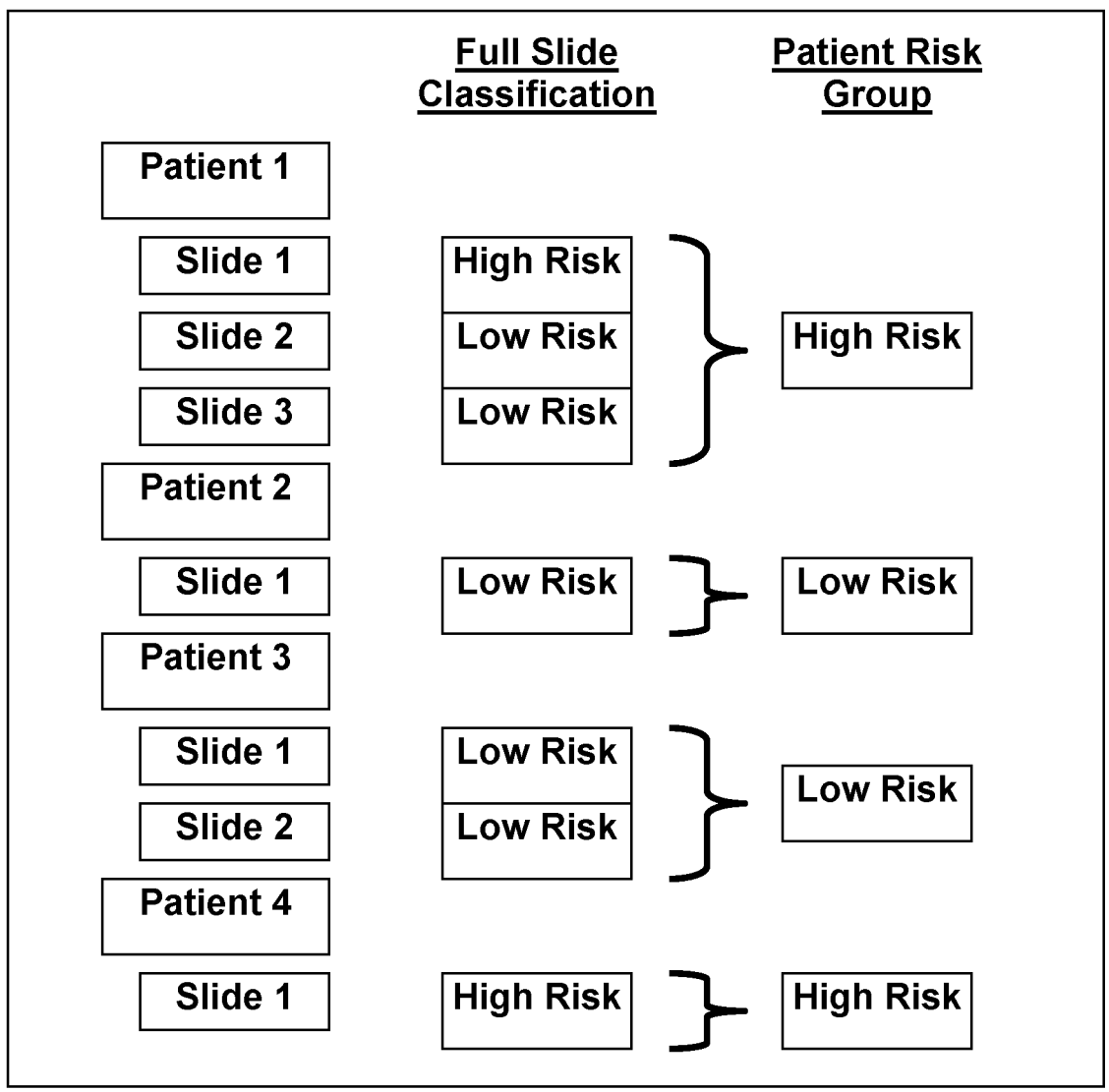
FIG. 7 illustrates an exemplary schematic of logic used to translate risk category of patient slides to patient risk.

This final feature-selected model was examined univariately through Kaplan-Meier curves and with multivariate analysis with common clinicopathological variables (comedo necrosis, size, grade, surgical margins, and patients age) using a Cox proportional hazard regression. This analysis was permed on patients rather than using the respective slides independently. For patients with multiple slides (n=127) in this cohort, any slide classification discordance (for example, one slide classified the patient for high risk while another did not) resulted in the patient being put in the high risk group 210. An exemplary schematic 700 of the logic used to translate risk category of patient slides to patient risk is shown in FIG. 7. Patients who possessed multiple resection slides were put into a high-risk subgroup if any of their slides were classified as high-risk by the recurrence classifier. An exemplary process 418 of the development of this classifier is depicted in FIG. 4. To develop the recurrence classifier the training slides 420 were first annotated 422 through the trained annotation classifier. The fully class-annotated slides 424 had whole slide features extracted 426, and selected 428 to identify the set of features that differed most significantly between patients who recurred and recurrence-free patients. The performance of these features within a classifier was determined through 5-fold cross validation 430, and the full training cohort was used to train a recurrence classifier 432. Further, this patient based model was tested within the high-grade cohort only, due to the clinical relevance, and between only patients who either received radiation or were treated with BCS alone, to determine the models predictive value on adjuvant therapy. The prediction of invasive recurrence within the risk groups was also analyzed.

Model Validation. To validate the recurrence classifier model's significant prognostic ability, we applied it to a second independent cohort of BCS-treated patients diagnosed with pure DCIS. The exact feature selected model and pipeline, as previously trained for both annotation and recurrence classification, was used on 199 slides (of 185 patients, which were not included in the training cohort). The patients predicted by the model to be in the high-risk group were compared with patients predicted to be at low recurrence risk through survival analysis (Kaplan-Meier and Cox regression) of their 10-year recurrence outcomes. As shown in the example illustrated in FIG. 4, the prognostic value of the pipeline was confirmed 434 on a validation cohort 436. Both the previously-trained annotation classifier 438 and recurrence classifier 444 were applied towards the patient samples 440 in this validation cohort, with whole slide feature extraction 442 and the resulting stratification of patients was evaluated 446.

Figure 8:
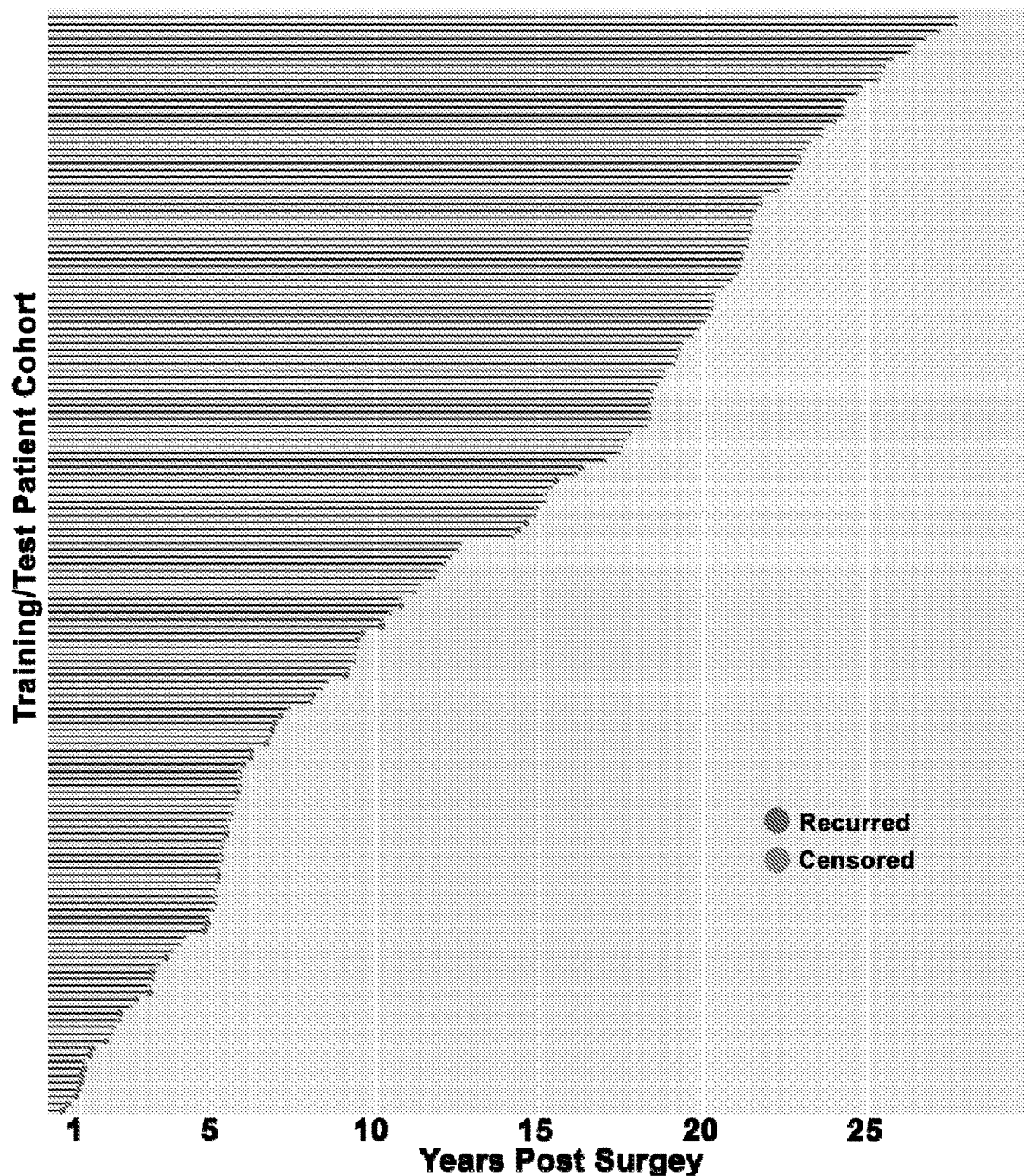
FIG. 8 illustrates recurrence distributions of the 159 patients in the training/test cohort, ordered according to earliest censored time or time of recurrence to last follow-up.

Training Data Cohort. In the current study, 159 patients (DCIS treated with BCS) were chosen, of which we obtained 335 scanned slides for training our model. The major characteristics for this patient cohort are shown in Table 4A. While the rate was low (23%), the majority (84%) of recurrence took place within the first 10 years of follow up, as shown in FIG. 8. FIG. 8 illustrates recurrence distributions of the 159 patients in the training/test cohort, ordered according to earliest censored time or time of recurrence to last follow-up. Red points indicate a recurrence at the last follow up date while green points specify censoring. Patients were generally high-grade (69%), post-menopausal (80.5%), older than 50 (83.7%), and were not subjected to radiation therapy (73.6%). Additionally, almost all patients had complete excision with wide negative margins (97.5%). Aside from an increased prevalence of high grade, patients who developed recurrence did not have any significant proportional differences of diagnostic clinicopathological variables from patients who remained recurrence free Table 4B.

TABLE 4

A
Training Cohort Overall Clinical Characteristics

| Baseline characteristic | Total (N = 159) |
|---|---|
| Patient age | |
| Median Age (range), years | 57 (30-83) |
| Age <50, n (%) | 26 (16.3) |
| Age >=50, n (%) | 133 (83.7) |
| Menopausal Status, n (%) | |
| Pre | 31 (19.5) |
| Post | 128 (80.5) |
| Presentation, n (%) | |
| Screening | 85 (53.5) |
| Symptomatic | 74 (46.5) |

TABLE 4-continued

| Comedo Necrosis, n (%) | |
|---|---|
| No | 60 (37.7) |
| Yes | 99 (62.3) |
| Radiation, n (%) | |
| No | 117 (73.6) |
| Yes | 42 (26.4) |
| Grade, n (%) | |
| 1 | 25 (15.8) |
| 2 | 24 (15.2) |
| 3 | 109 (69.0) |
| Margins, n (%) | |
| Negative | 154 (97.5) |
| Positive | 4 (2.5) |
| Tumor Size | |
| Median Tumor Size | 1.7 (0.1-14.5) |
| Size <2.0, n (%) | 88 (56.4) |
| Size >=2.5, n (%) | 68 (43.6) |
| Recurrence status, n (%) | |
| Recurrence free | 122 (76.7) |
| Recurred | 37 (23.3) |

B
Training Cohort Clinical Characteristics by Recurrence Status

| Baseline characteristic | Recurred (N = 37) | Rec. Free (N = 122) | p value |
|---|---|---|---|
| Patient age | | | |
| Median Age (range), years | 55 (41-73) | 57 (30-83) | 0.3225 |
| Age <50, n (%) | 8 (21.6) | 18 (14.7) | |
| Age >=50, n (%) | 29 (78.4) | 104 (85.3) | |
| Menopausal Status, n (%) | | | |
| Pre | 9 (24.3) | 22 (18.0) | 0.3975 |
| Post | 28 (75.7) | 100 (82.0) | |
| Presentation, n (%) | | | |
| Screening | 16 (43.2) | 69 (56.6) | 0.155 |
| Symptomatic | 21 (56.8) | 53 (43.4) | |
| Comedo Necrosis, n (%) | | | |
| No | 15 (40.5) | 45 (36.9) | 0.6878 |
| Yes | 22 (59.5) | 77 (63.1) | |
| Radiation, n (%) | | | |
| No | 28 (75.7) | 89 (72.9) | 0.7419 |
| Yes | 9 (24.3) | 33 (27.1) | |
| Grade, n (%) | | | |
| 1 | 1 (2.7) | 24 (19.8) | 0.0425 |
| 2 | 7 (18.9) | 17 (14.1) | |
| 3 | 29 (78.4) | 80 (66.1) | |
| Margins, n (%) | | | |
| Negative | 35 (94.6) | 119 (98.3) | 0.2035 |
| Positive | 2 (5.4) | 2 (1.7) | |
| Tumor Size | | | |
| Median Tumor Size | 1.5 (0.3-5.0) | 1.8 (0.1-14.5) | 0.3022 |
| Size <2.0, n (%) | 23 (63.9) | 65 (54.2) | |
| Size >=2.5, n (%) | 13 (36.1) | 55 (45.8) | |

Table 4A shows descriptive data detailing the train/test cohort's clinicopathological variables. Table 4B shows the distribution of baseline characteristic between patients who experienced recurrences versus those that did not. The $\chi 2$ p value signifies significant difference in proportions.

Figure 9:
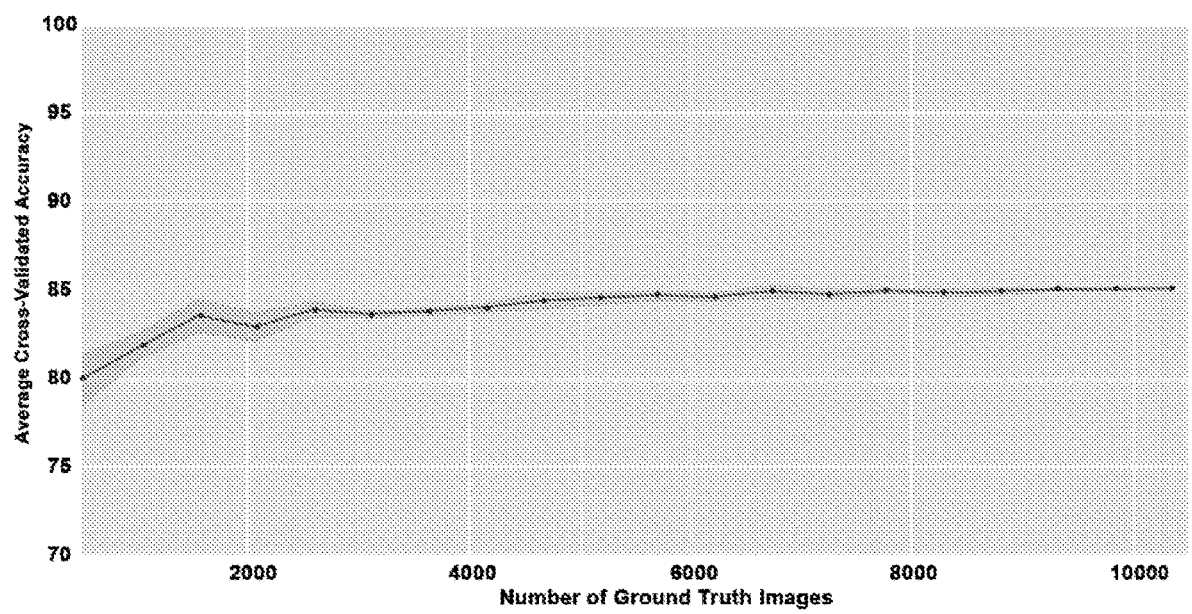
FIG. 9 illustrates the effect of sample size used for ground truth annotation on cross-validated accuracy.

Tissue Annotation To develop a pipeline for automated annotation of various clinically relevant regions [stroma, adjacent nonmalignant epithelial ducts, cancerous ducts, stromal regions with large immune (lymphocyte) infiltration, and blood vessels] within DCIS tumor tissue sections, we found that overall accuracy leveled off at 10,359 50×50 pixel ground truth windows, as shown in FIG. 9, from 32 training cohort slides. FIG. 9 illustrates the effect of sample size used for ground truth annotation on cross-validated accuracy. Average k-fold accuracy of annotation prediction versus number of ground truth regions. Shaded bands represent 95% confidence intervals.

For developing the final annotation classifier, these ground truth areas were augmented (using rotation/transposition) to a total of 41,436 1002, shown in FIG. 10. FIG. 10 illustrates an example of full slide annotation. A list of annotation classes used, and relative example, alongside the number of ground truth regions selected to develop the texture based classifier is shown 1002. While using the original (non-augmented) collection of ground truth regions, a majority of texture features observed possessed significant discriminatory ability between all annotated class combinations 1004. Multivariate adjusted p-value (Tukey-Kramer) distributions for all 160 features between all annotated class comparisons 1004 are shown. A reference line 1005 indicating an adjusted p-value of 0.05 is shown alongside the number (and percentage) or features which do not show significant discriminatory ability. Classification with 32-fold cross validation of the original collection resulted in an accuracy of 84.59%, with individual class distinctions ranging from 75.8%-90.5% (not counting background) 1006. A confusion matrix 1006 compares training data ground truth to the cross validated annotation classifier test set outputs. Analysis was performed on the original regions before ×4 augmentation.

Figure 11:
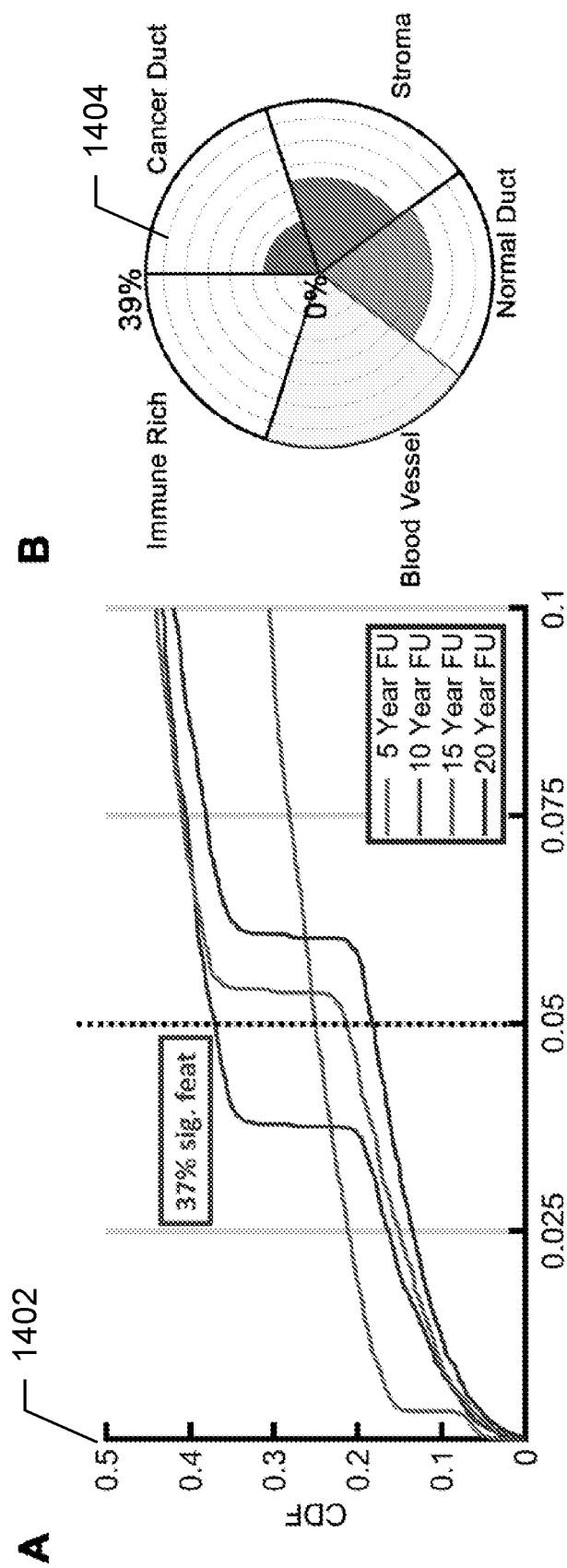
FIG. 11 illustrates an example of the cumulative density function (CDF) of feature significance.

Whole Slide Analysis and Recurrence Prediction. Thresholding at a 10 year follow up maximized the amount of significant whole slide features different between slides from patients who recurred versus those that did not progress. FIG. 11 illustrates an example of the cumulative density function (CDF) 1102 of feature significance, noted by the t-test p-values, versus maximum follow-up (FU) time explored. Using 10-year recurrence, 37% of whole slide features were significantly (0.05) different between patients who developed recurrence by 10 years versus those that remained recurrence-free. This follow up time is also consistent with many follow up times in clinical studies and with the fact that most patients recur within 10 years, Overall, around 1,238 (37%) of whole slide features were significant (p<0.05) with a 10 year follow up as compared to at most 25% for 5,15, and 20-year follow-up time points.

FIG. 12 illustrates an example of full slide feature selection. The change in model accuracy and high-risk group hazard ratio with the sequential addition of features 1202 is shown. The reference hazard ratio and accuracies, based on the model with all features, is shown in red and blue dashed lines respectively. The model which included all filtered features (Sig*: p<0.05) is also shown for comparison. Bars on markers indicate 95% confidence intervals. A model built with these filtered features resulted in an average 5-fold cross validated accuracy of 80.8% and a high-risk group possessing a hazard ratio of 3.19 1202, almost equivalent to the performance of using the full feature set (ACC: 80.8% and HR: 3.13). Between the significant 10-whole slide features, the majority (88%) stem from non-cancer annotations (though almost none [1%] come from differences in lymphocyte dense properties between patients) As shown in the example 1104 illustrated in FIG. 11, within this 10-year follow-up recurrence distinction, the significant feature distribution by class difference is shown in a radar plot, with the max fill (blood vessel features) indicating 39% of the filtered total significant features.

Feature characteristics of the final models feature set 1204 are shown. The significance is based on the basic t-test between each feature and patients who experienced recurrence within 10 years and those that did not. The misclassification cost is computed sequentially (For example, for the feature 3 misclassification cost, it's for a model which is developed with features 1 and 2 as well). Testing 10-year recurrence risk model built with these filtered features (i.e. using all significant features prior to the sequential removal 206, shown in FIG. 2, resulted in an average 5-fold cross validated accuracy around 80%, regardless of the ML model, as shown in Table 5, and a random forest high-risk group possessing a hazard ratio of 3.19 1202, almost equivalent to the performance of using the full feature set (accuracy: 80.8%; HR: 3.13). Table 5 shows a comparison of multiple machine learning algorithms to select the best model (and its associated features) for the recurrence classifier. 'No annotation' indicates the performance of a random forest model built without considering classes obtained from the first annotation step. Optimized models reflect performance after selection of optimal set of features. For each ML model, the model accuracy and high-risk group hazard ratio upon using either the full feature set or the optimized feature set, are shown

TABLE 5

| Model | Average Accuracy (std.) | Average Hazard Ratio (std.) |
|---|---|---|
| Optimized Random Forest (RF) | 0.86 (0.010) | 8.55 (1.272) |
| Full Feature Non Annotated RF | 0.78 (0.012) | 3.08 (0.496) |
| Optimized Non Annotated RF | 0.79 (0.008) | 2.82 (0.283) |
| Full Feature SVM Model | 0.80 (0.002) | 1.21 (0.174) |
| Optimized SVM Model | 0.80 (0.037) | 7.27 (4.537) |
| Full Feature KNN Model | 0.79 (0.004) | 1.59 (0.347) |
| Optimized KNN Model | 0.80 (0.009) | 4.31 (0.537) |

Choosing the most prognostic variables through the sequential forward selection, though, resulted in half of the features being derived from cancer areas 1204, shown in FIG. 12, with additional details shown in Table 6. In the example shown in Table 6, the distribution of baseline characteristics between patients who experienced ipsilateral recurrences versus those that did not is shown. The ×2 p value signifies significant difference in proportions.

TABLE 6

Training Cohort Clinical Characteristics by Recurrence Status

| Baseline characteristic | Recurred (N = 37) | Rec. Free (N = 122) | p value |
|---|---|---|---|
| Patient age | | | |
| Median Age (range), years | 55 (41-73) | 57 (30-83) | 0.3225 |
| Age <50, n (%) | 8 (21.6) | 18 (14.7) | |
| Age >=50, n (%) | 29 (78.4) | 104 (85.3) | |
| Menopausal Status, n (%) | | | |
| Pre | 9 (24.3) | 22 (18.0) | 0.3975 |
| Post | 28 (75.7) | 100 (82.0) | |
| Presentation, n (%) | | | |
| Screening | 16 (43.2) | 69 (56.6) | 0.155 |
| Symptomatic | 21 (56.8) | 53 (43.4) | |

TABLE 6-continued

Training Cohort Clinical Characteristics by Recurrence Status

| Baseline characteristic | Recurred (N = 37) | Rec. Free (N = 122) | p value |
|---|---|---|---|
| Comedo Necrosis, n (%) | | | |
| No | 15 (40.5) | 45 (36.9) | 0.6878 |
| Yes | 22 (59.5) | 77 (63.1) | |
| Radiation, n (%) | | | |
| No | 28 (75.7) | 89 (72.9) | 0.7419 |
| Yes | 9 (24.3) | 33 (27.1) | |
| Grade, n (%) | | | |
| 1 | 1 (2.7) | 24 (19.8) | 0.0425 |
| 2 | 7 (18.9) | 17 (14.1) | |
| 3 | 29 (78.4) | 80 (66.1) | |
| Margins, n (%) | | | |
| Negative | 35 (94.6) | 119 (98.3) | 0.2035 |
| Positive | 2 (5.4) | 2 (1.7) | |
| Tumor Size | | | |
| Median Tumor Size | 1.5 (0.3-5.0) | 1.8 (0.1-14.5) | 0.3022 |
| Size <2.0, n (%) | 23 (63.9) | 65 (54.2) | |
| Size >=2.0, n (%) | 13 (36.1) | 55 (45.8) | |

The final 8 feature model lowered the misclassification rate to 101, achieved an average (of 100 iterations) cross validated accuracy above 86%, and returned a model with an average high-risk group with an 8.4× higher chance of relative recurrence risk by 10 years 1202. A typical Kaplan Meier survival curve 1206 from one of the model training iterations (out of the total 100) of the combined cross-validated test sets is shown. The Kaplan-Meier curves of the final model stratification on slides used for the training cohort were developed by combining the testing sets for the select cross validated iteration. The significance is measured through the log-rank test. The slides classified into the high risk group carry a recurrence free survival (RFS) of only 24% compared to the 90% seen in the low risk group. To show the importance of the annotation step, a full slide RFS model built with feature selection without first considering the previously predicted annotations (using the overall texture statistical moments of the slides) resulted in a significantly lower accuracy (79%) and HR (2.82) Table 7 shows additional feature details for final 8-feature set in the DCIS 10-year recurrence risk classifier.

TABLE 7

Figure 13:
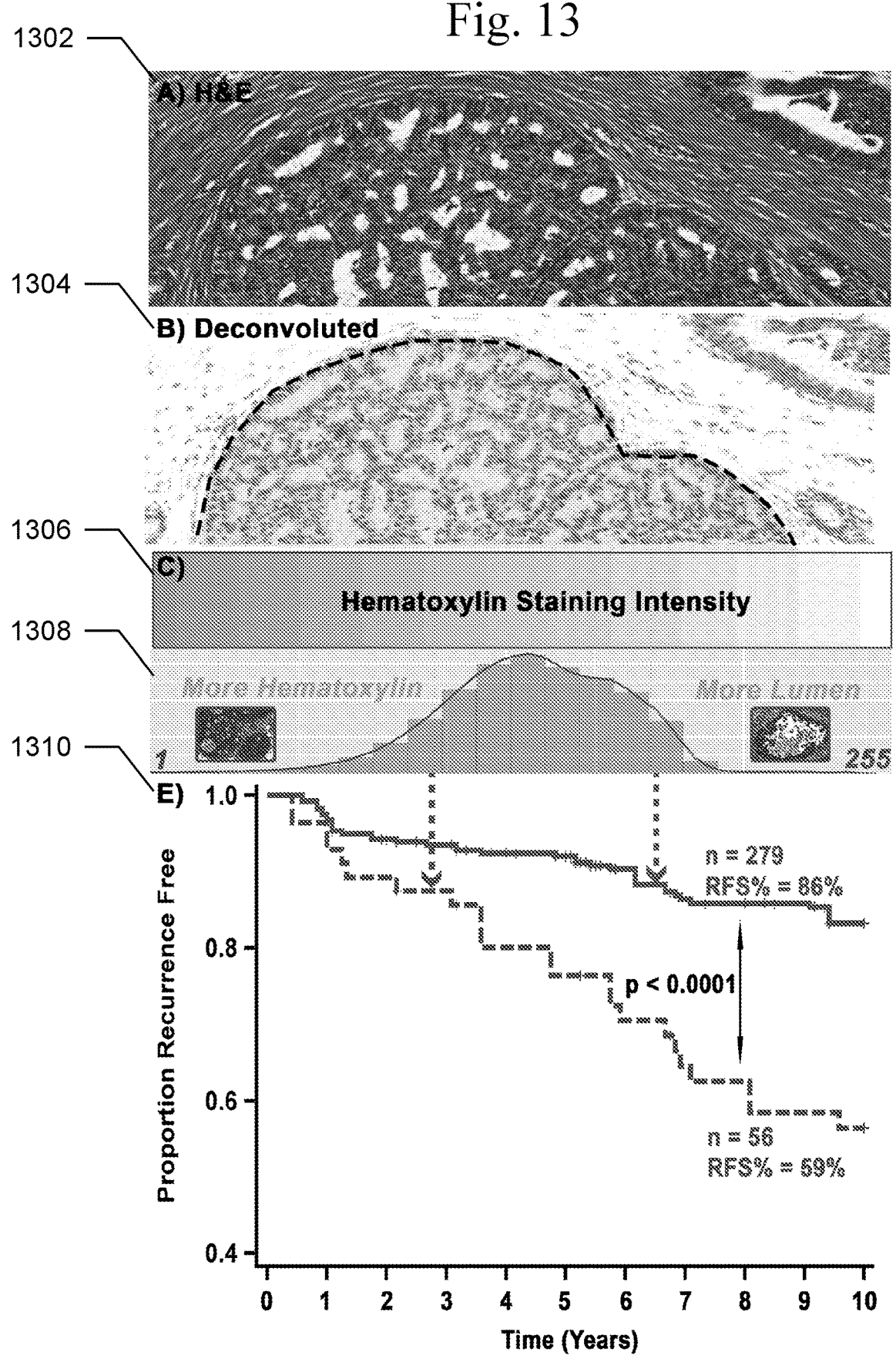
FIG. 13 illustrates an example of interpretation and prognostic relevance of the top predictive feature according to embodiments of the present systems and methods.
Figure 14A:
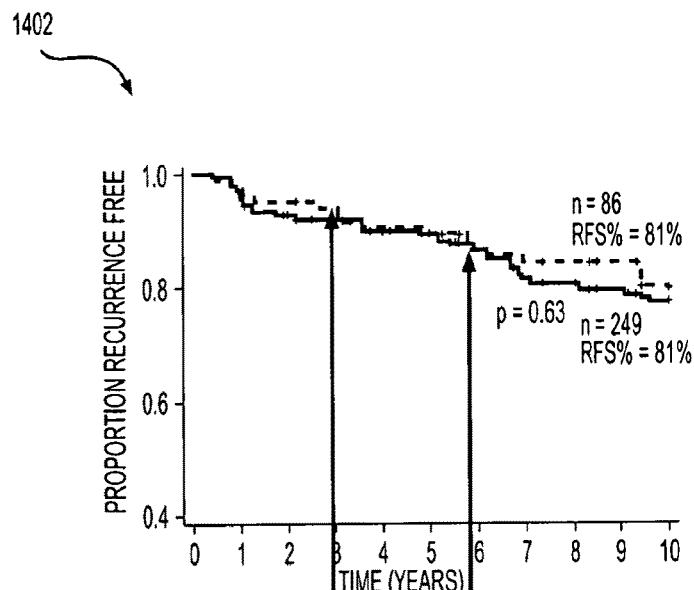
FIG. 14 illustrates an example of the combination of features to produce optimal stratification.
Figure 14B:
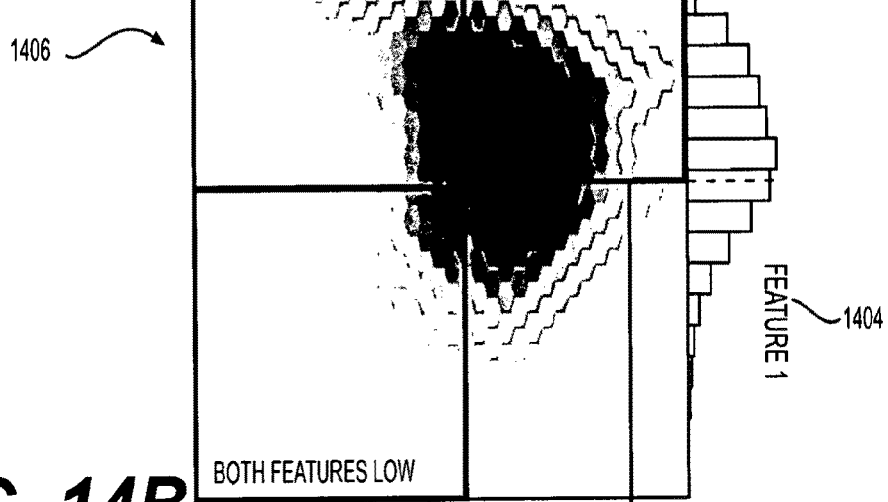
Figure 14C:
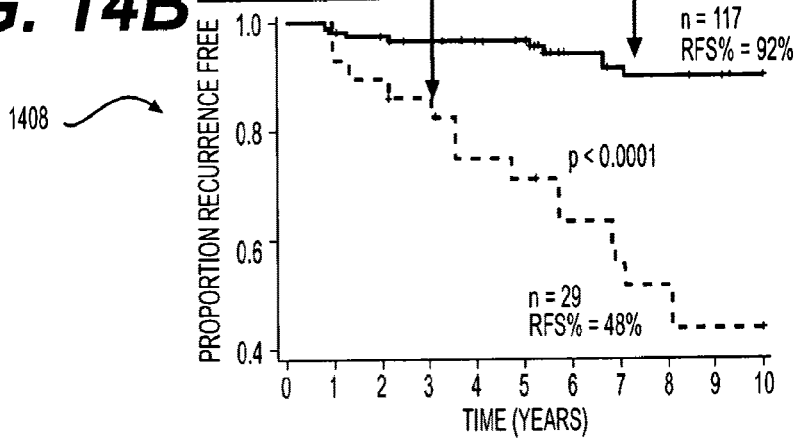

Feat 1: Mean pixel expression over the 4th Otsu threshold
Feat 2: Number of pixels between the 5th and 6th Otsu thresholds
Feat 3: Short Run High Gray-Level Emphasis at 135 degrees
Feat 4: Short Run High Gray-Level Emphasis horizontally
Feat 5: Mean amplitude of the gabor filter(horizontal orientation and wavelength of 13 pixels)
Feat 6: Contrast of pixels at 135 degrees
Feat 7: Mean amplitude of the gabor filter (120 degree orientation and wavelength of 13 pixel)
Feat 8: Contrast of pixels horizontally Univariate HR of the selected features, z-score transformed for illustrative purposes 1208. All variables are significant with 95% confidence intervals with bars not crossing the 1.0 reference point. These features, as continuously univariate variables, all provided significant prognostic value, with half being associated with recurrence while the other half provide a protective effect 1208. Dichotomizing patients into groups using the mean cancer features (1 and 3), for interpretive purposes, showed conflicting effectiveness. Alone, feature 1 very significantly separated patients into two distinct risk groups, as shown in FIG. 13, while feature 3 was unable to retain significance, as shown in the example of FIG. 14, at 1402. FIG. 14 illustrates an example of the combination of features to produce optimal stratification. However, if patients were first split into high and low groups through feature 1 1404 followed by another stratification using feature 3 1406, a significant difference could be recovered 1408. This shows that a combination of features produces improved stratification.

FIG. 13 illustrates an example of interpretation and prognostic relevance of the top predictive feature: The average deconvoluted intensity (after using a large Otsu threshold) of cancer annotated regions. An example regions of a cribriform architecture in H&E 1302 and after hematoxylin deconvolution 1304. Intense staining (relative to the window section) is represented by a grey level intensity of 1, while no staining is depicted by a grey level value of, for example, 255 1306. The adaptive Otsu thresholds by progressively using a higher threshold. Therefore, if the cancer region has sparse and soft hematoxylin staining, indicating more luminal spacing, it would contain a higher average intensity as compared to a solid pattern. Using an optimized threshold of, for example, 208 1308, it's observed that full slides whose cancer regions have an average value above that cutoff recur significantly less than patients below that threshold 1310.

Figures 15A, 15B:
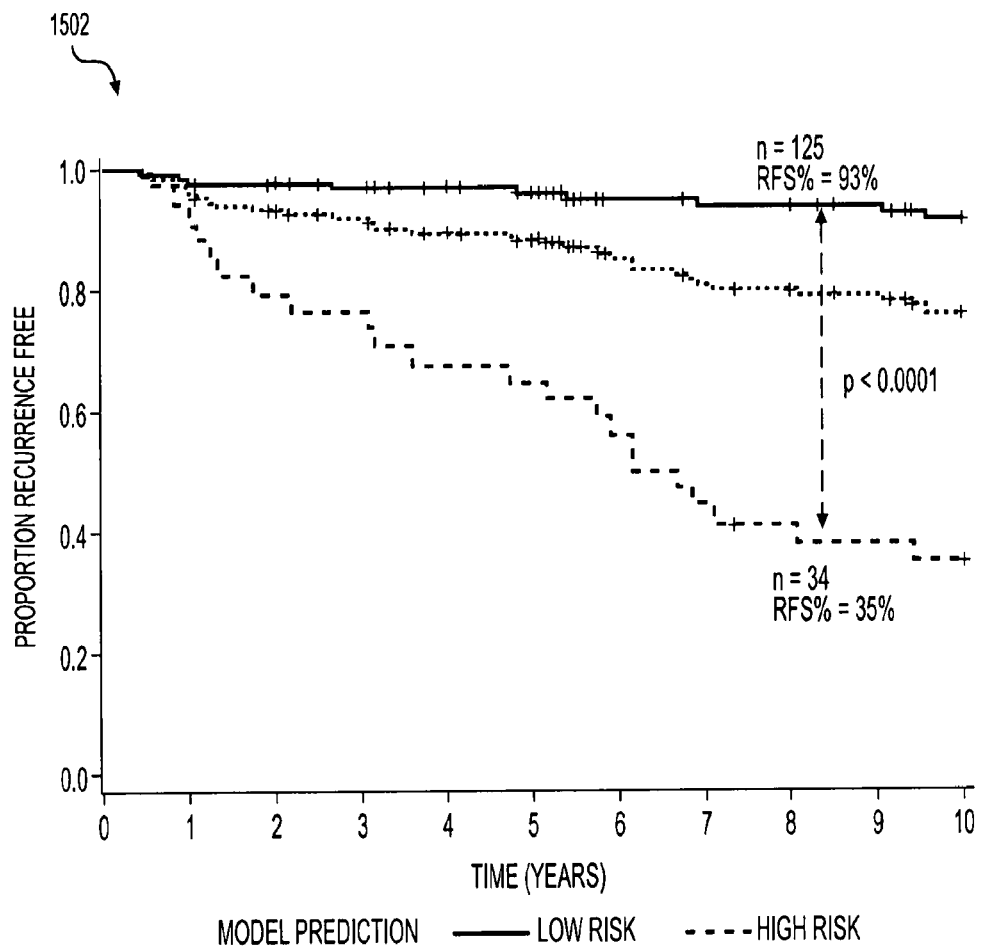
FIG. 15 illustrates univariate and multivariate analysis of the prediction model on the training cohort.

Applying the recurrence classifier based on the final 8 features at the patient level showed that the classifier significantly stratified the patients in the training cohort (P<0.0001). FIG. 15 illustrates univariate and multivariate analysis of the prediction model on the training cohort. Cross validated Kaplan-Meier curves 1502 of the training cohort developed by combining the testing sets for the select cross validated iteration are shown. The significance is measured through the log-rank test and the grey line represents the un-stratified full cohort. Univariate and multivariate Cox regression analysis 1504 comparing the influence of common clinicopathological variables alongside the predictive 8 feature model, for recurrence free survival, on the cross validated test sets of the training data are shown. Patients classified to the high risk group (N=34) had a RFS of only 35%, compared to the 93% seen in patients in the low risk group (N=125) 1502, shown in FIG. 15. This iteration had a univariate high-risk hazard ratio of 11.6 and retained its very high significance when controlling for necrosis, size, grade, margins, radiation therapy, and patient age 1504. None of the clinical variables in the original cohort showed significant risk stratification ability univariately 1504.

FIG. 16 illustrates an example of stratification of patients in the training cohort using standard clinical variables. FIG. 16 shows cross validated Kaplan-Meier curves of patient outcomes (Recurrence-free survival, RFS) stratified based on tumor size 1602, patient age 1604, comedo necrosis status 1606, and Nottingham grade 1608. Significance is measured through the log-rank test.

Figure 17:
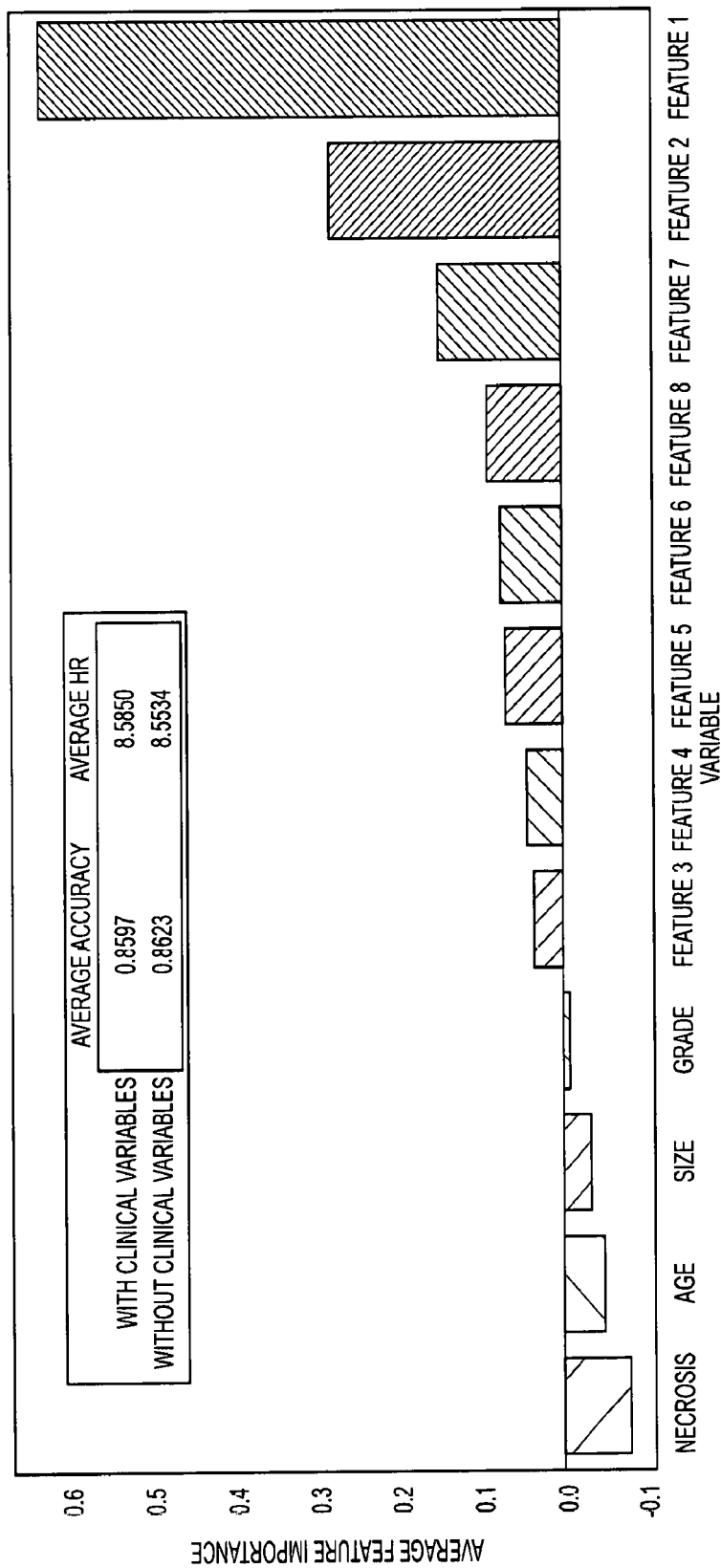
FIG. 17 illustrates an example of the impact of clinical features on model performance.

Additionally, select clinical variables neither improved the overall model nor add any prognostic relevance individually, as shown in the example illustrated in FIG. 17. FIG. 17 illustrates an example of the impact of clinical features on model performance when clinical variables are concatenated with the 8 features of the recurrence classifier, within a random forest model. Averaged out-of-bag feature importance (and 95% confidence intervals) from 100 models shows that clinical features do not contribute positively to the overall performance of the model. Feature importance (i.e., how heavily the model relies on each given feature for the output prediction) is defined as the change in prediction error when the values of those variables are permuted (to, in effect, break the relationship between the feature and the model outcome) across out-of-bag observations. Hence larger error changes correspond to more vital variables. The average cross-validated accuracy significantly decreased when clinical variables were used and hazard ratios of models built with and without clinical variables showed no significant differences.

FIG. 18 illustrates an example of cross validated Kaplan-Meier curves of patients within the training cohort, developed by combining the testing sets for a cross validated iteration. Interestingly, the same model was able to significantly stratify high grade DCIS patients 1802 (showing the recurrence classifier model was used with Grade 3 patients' slides only), patients who received adjuvant radiation therapy 1804 (showing the recurrence classifier used on slides from patients who received adjuvant radiation), and those treated with BCS alone 1806 into subgroups with high and low recurrence risks. Additionally, the model was able to identify patients at high-risk for invasive recurrence 1808. Significance was measured through the log-rank test.

Validation. Relative to the training cohort, patients in the validation cohort were all grade 3, had higher rates of comedo necrosis (81.6%, p<0.0001), and slightly higher presentation at screening (64.9%, p=0.0316) as shown in Table 8, but otherwise possessed similar descriptive characteristics as shown in Table 9. Table 8 shows an example of the distribution of baseline characteristics between patients who experienced recurrence versus those that did not. The $\chi2$ p-value signifies significant difference in proportions.

TABLE 8

Validation Cohort Clinical Characteristics by Recurrence Status

| Baseline characteristic | Recurred (N = 32) | Rec. Free (N = 153) | p value |
|---|---|---|---|
| Patient age | | | |
| Median Age (range), years | 60 (44-73) | 59 (36-77) | 0.5643 |
| Age <50, n (%) | 3 (9.4) | 20 (13.1) | |
| Age >=50, n (%) | 29 (90.6) | 133 (86.9) | |
| Menopausal Status, n (%) | | | |
| Pre | 5 (15.6) | 24 (15.7) | 0.9931 |
| Post | 27 (84.4) | 129 (84.3) | |
| Presentation, n (%) | | | |
| Screening | 20 (62.5) | 100 (65.4) | 0.758 |
| Symptomatic | 12 (37.5) | 53 (34.6) | |
| Comedo Necrosis, n (%) | | | |
| No | 8 (25.0) | 26 (17.0) | 0.2876 |
| Yes | 24 (75.0) | 127 (83.0) | |
| Radiation, n (%) | | | |
| No | 30 (93.8) | 115 (75.2) | 0.0202 |
| Yes | 2 (6.2) | 38 (24.8) | |
| Grade, n (%) | | | |
| 1 | 0 (0) | 0 (0) | — |
| 2 | 0 (0) | 0 (0) | |
| 3 | 32 (100) | 153 (100) | |
| Margins, n (%) | | | |
| Negative | 32 (100) | 151 (98.7) | 0.5155 |
| Positive | 0 (0) | 2 (1.3) | |

TABLE 8-continued

Validation Cohort Clinical Characteristics by Recurrence Status

| Baseline characteristic | Recurred (N = 32) | Rec. Free (N = 153) | p value |
|---|---|---|---|
| Tumor Size | | | |
| Median Tumor Size | 1.7 (0.2-12.0) | 1.8 (0.3-11.0) | 0.3233 |
| Size <2.0, n (%) | 20 (62.5) | 81 (52.9) | |
| Size >=2.0, n (%) | 12 (37.5) | 72 (47.1) | |

Table 9 shows an example of proportional differences in variable distributions between the training/testing cohort and the external validation cohort. P-values are for the chi-square test for proportions.

TABLE 9

| Baseline characteristic | p value |
|---|---|
| Recurrence | 0.1294 |
| Radiation | 0.2982 |
| Margins | 0.3071 |
| Comedo Necrosis | <.0001 |
| Grade | <.0001 |
| Presentation | 0.0316 |
| Menopausal Status | 0.3518 |
| Size | 0.7368 |
| Age | 0.2997 |

Figure 19:
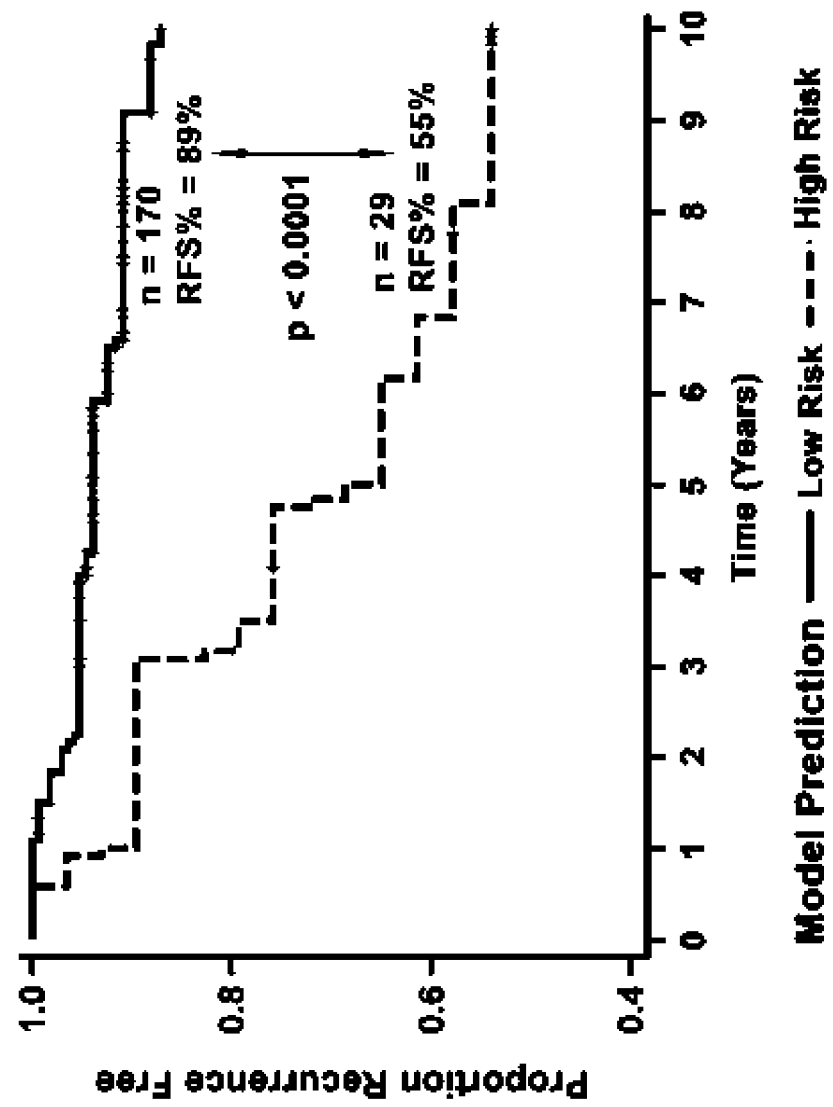
FIG. 19 shows an example of Kaplan-Meier curves of slides within the validation cohort stratified by the trained recurrence classifier model.

Analyzing individual slides (treating each slide as an individual patient) using previously trained classifier resulted in highly stratified risk groups using bivariate high and low risk, as shown in FIG. 19. FIG. 19 shows an example of Kaplan-Meier curves of slides within the validation cohort stratified by the trained recurrence classifier model. Significance is measured through the log-rank test.

Analyzing patients led to additional improvement in prognosis classification. Even with very few patients recurring after radiotherapy in this cohort, the model was still able to significantly predict patient response, as shown at 2002 of FIG. 20. FIG. 20 illustrates an example of cross validated Kaplan-Meier curves of patients within the validation cohort, developed by combining the testing sets for a cross validated iteration. Recurrence classifier model was used on slides from patients who received adjuvant radiation 2002. Additionally, patients treated with only BCS showed a clear high risk group 2004. Censoring the 8 patients whose recurrence was DCIS, rather than invasive, resulted in similar levels of risk group stratification 2006.

Figures 21A, 21B:
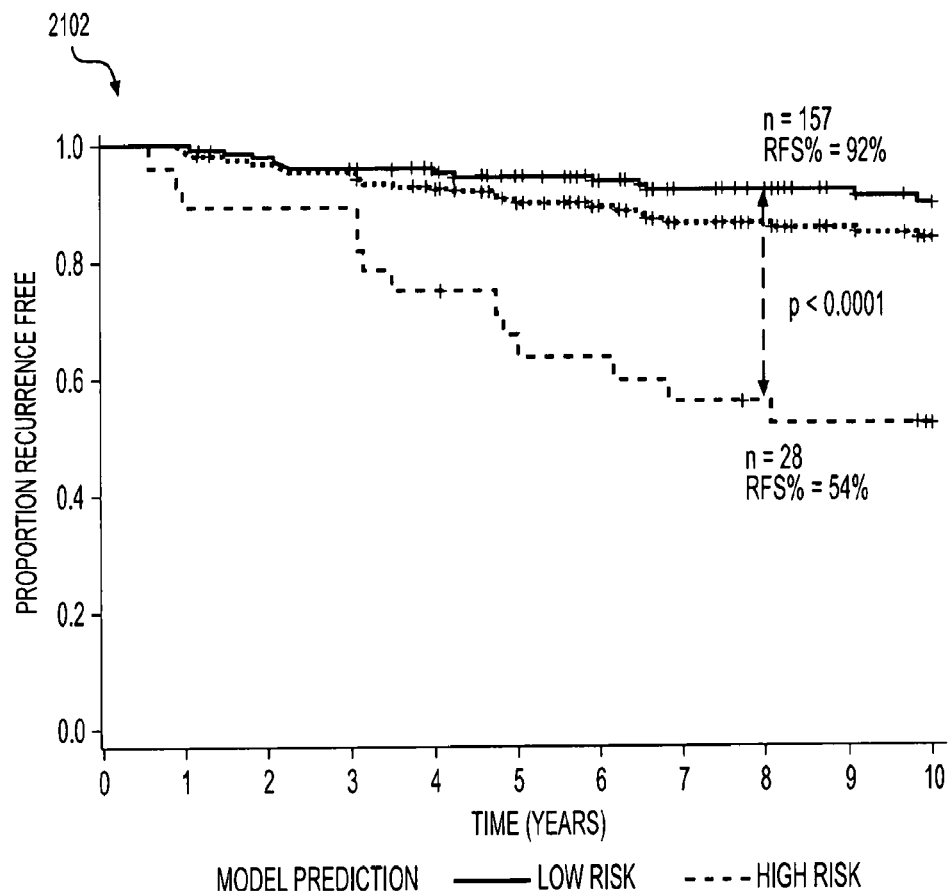
FIG. 21 illustrates an example of model validation.

FIG. 21 illustrates an example of model validation: Kaplan-Meier curves 2102 of models stratification on patients in the validation cohort are shown. The significance is measured through the log-rank test and the grey line represents the un-stratified full cohort. Univariate and multivariate Cox regression analysis 2104 comparing the influence of common clinicopathological variables alongside the predictive 8 feature model, for 10 year recurrence free survival, on the validation cohort are shown. Nighty-two percent of patients classified into the low risk stay recurrence free within 10 years, compared to only 54% of patients who are classified as high risk 2102. While lower than the training/test cohort, the univariate hazard ratio of this classifier on the validation patients is 6.4 (p<0.0001) and over 6.8 (p<0.0001) when controlling for necrosis, size, margin status, and age 2104.

While a very limited proportion of women with DCIS die from the original disease, the onset of invasive ipsilateral recurrence leads to an immense relative risk of mortality. Unfortunately, limited understanding of progression of pre-invasive ductal lesions to invasion and lack of clinicopathological and molecular markers, which could predict recurrence, leads to doubt in therapy. While breast-conserving surgery (BCS) is the most common surgical treatment for DCIS, there is no consensus among pathologists for the use of adjuvant radiation therapy, even for DCIS tumors in low grade and size. Without a confident measure of risk, patients are often at risk for both over and under treatment, while therapists are left having to balance risks potentially associated with radiation that sometimes only shows marginal benefit.

Embodiments of the present systems and methods may provide a novel 2 portion image analysis pipeline which could function as a personalized prognostic tool to determine the risk of 10 year recurrence of patients treated with BCS. The first portion 100 may allow for classification of each region of the surgical dissection into clinically significant annotations through 166 hematoxylin texture features. The second portion 200 may use the statistical moments of select features and regions from the full slide to provide a 10-year recurrence risk (high versus low) that would allow for more informed treatment decisions.

Embodiments may employ H&E, while other embodiments may employ CD34 or CD31 staining, alongside a smaller sliding window, which may uncover small, but relevant, vascularization. As our use of the 'normal' annotation is inclusive of everything but DCIS, they often pick up abnormal, and potentially prognostic, malignancy precursors. Proliferative, non-cancerous, alterations such as columnar cell lesions are often seen alongside patients diagnosed with DCIS, suggesting their potential for malignant transformations and can be used as a marker for breast cancer risk.

Embodiments may create a model, which may provide improved prognostic ability, outperforming histopathological variables such as grade, age, margin status, and tumor size. Within the externally validated cohort, consisting of high grade DCIS patients of whom the majority were treated with BCS alone, the model was able to identify a high risk group of patients that had almost a 50% chance of recurring within 10 years (versus <10% chance within the low risk group). Within the subsets of patients treated with BCS alone or those receiving additional adjuvant radiation, the model also identified the cohorts likely to recur. Taken together, this implies that this method can identify a) patients whose recommendation should be escalated to include radiation or mastectomy b) patients who will not respond to radiation and should be candidates for mastectomy and c) patients who can be safely treated with BCS alone.

On, for example, a Dell Precision T5610 computer, our pipeline takes about 8 minutes to process a full slide. It extracts information from the full slide, which allows it to incorporate many biologically relevant classes of regions, multiple cancer foci, and intertumor diversity stemming from mixtures of many cell grades. As an automated non-stochastic pipeline, it suffers from no interobserver error, which may plague some pathological grading, and also introduces the potential to use the pipeline for other solid tumors with minimal adjustment (augmenting new tissue classes or identifying most relevant features for that cancer).

Figure 22:
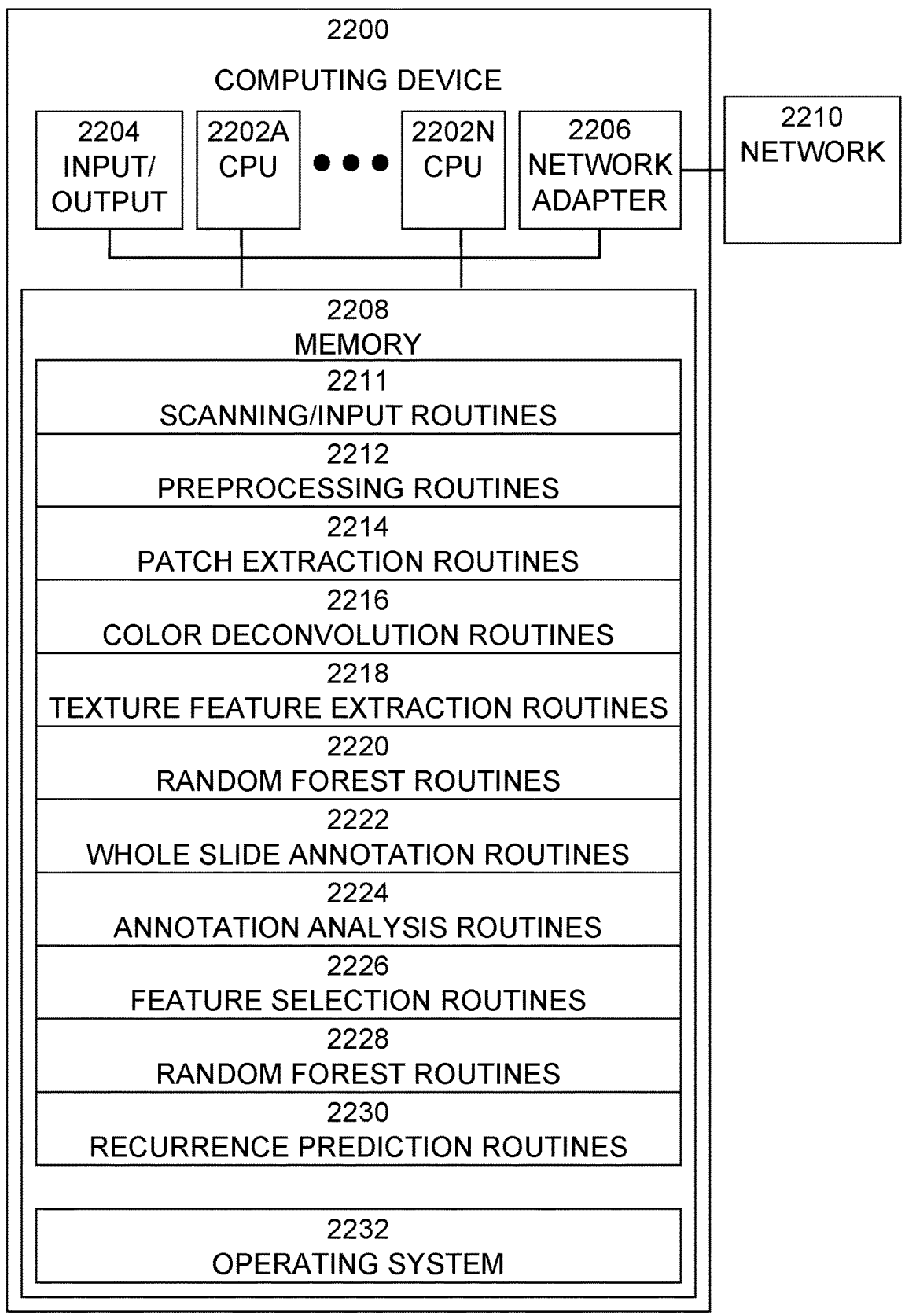
FIG. 22 is an exemplary block diagram of a computer system, in which processes involved in the embodiments described herein may be implemented.

An exemplary block diagram of a computer system 2202, in which processes involved in the embodiments described herein may be implemented, is shown in FIG. 22. Computer system 2202 may be implemented using one or more programmed general-purpose computer systems, such as embedded processors, systems on a chip, personal computers, workstations, server systems, and minicomputers or mainframe computers, or in distributed, networked computing environments. Computer system 2202 may include one or more processors (CPUs) 2202A-2202N, input/output circuitry 2204, network adapter 2206, and memory 2208. CPUs 2202A-2202N execute program instructions in order to carry out the functions of the present communications systems and methods. Typically, CPUs 2202A-2202N are one or more microprocessors, such as an INTEL CORE® processor. FIG. 22 illustrates an embodiment in which computer system 2202 is implemented as a single multi-processor computer system, in which multiple processors 2202A-2202N share system resources, such as memory 2208, input/output circuitry 2204, and network adapter 2206. However, the present communications systems and methods also include embodiments in which computer system 2202 is implemented as a plurality of networked computer systems, which may be single-processor computer systems, multi-processor computer systems, or a mix thereof.

Input/output circuitry 2204 provides the capability to input data to, or output data from, computer system 2202. For example, input/output circuitry may include input devices, such as keyboards, mice, touchpads, trackballs, scanners, analog to digital converters, etc., output devices, such as video adapters, monitors, printers, etc., and input/output devices, such as, modems, etc. Network adapter 2206 interfaces device 2200 with a network 2210. Network 2210 may be any public or proprietary LAN or WAN, including, but not limited to the Internet.

Memory 2208 stores program instructions that are executed by, and data that are used and processed by, CPU 2202 to perform the functions of computer system 2202. Memory 2208 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 2208 may vary depending upon the function that computer system 2202 is programmed to perform. In the example shown in FIG. 22, exemplary memory contents are shown representing routines and data for embodiments of the processes described above. However, one of skill in the art would recognize that these routines, along with the memory contents related to those routines, may not be included on one system or device, but rather may be distributed among a plurality of systems or devices, based on well-known engineering considerations. The present communications systems and methods may include any and all such arrangements.

In embodiments, at least a portion of the software shown in FIG. 22 may be implemented on a current leader server. Likewise, in embodiments, at least a portion of the software shown in FIG. 22 may be implemented on a computer system other than the current leader server.

In the example shown in FIG. 22, memory 2208 may include scanning/input routines 2211, preprocessing routines 2212, patch extraction routines 2214, color deconvolution routines 2216, texture feature extraction routines 2218, random forest routines 2220, whole slide annotation routines 2222, annotation analysis routines 2224, feature selection routines 2226, random forest routines 2228, recurrence prediction routines 22830, and operating system 22832. Scanning/input routines 2211 may include software routines to scan histology images and to input the images into the processing pipeline. Preprocessing routines 2212 may include software routines to preprocess an image slide through whole slide color normalization and down-sampling. Patch extraction routines 2214 may include software routines use a sliding window to extract patches of the preprocessed slide. Color deconvolution routines 2216 may include software routines to color deconvolute the patches to a hematoxylin layer. Texture feature extraction routines 2218 may include software routines to extract values for texture features from the patches. Random forest routines 2220 may include software routines to perform random forest processing (prior to whole slide annotation processing), which may output a probability of each patch belonging to a specific category (malignant duct, immune rich stroma, non-immune rich stroma, non-cancerous duct, and blood vessel). Whole slide annotation routines 2222 may include software routines to combine patch probabilities to produce a whole slide annotation. Annotation analysis routines 2224 may include software routines to analyze each annotation through feature distributions, spatial features which compare distances between different classes, and other features such as region confidence. Feature selection routines 2226 may include software routines to select a final feature list. Random forest routines 2220 may include software routines to perform random forest processing (prior to recurrence prediction processing). Recurrence prediction routines 22 2230 may include software routines use the final feature list to train a random forest classifier to predict high-versus low-risk of recurrence and to provide a recommendation of additional therapy. Operating system 22 2232 may provide overall system functionality.

As shown in FIG. 22, the present communications systems and methods may include implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multi-tasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A computer-implemented method for determining treatment of a patient, the method comprising:
    receiving an image of living tissue of a patient, the image comprising a stained histopathology slide;
    annotating, via a whole slide annotation routine, the entire image into tissue structures, wherein the whole slide annotation routine includes at least one preprocessing routing to preprocess the stained histopathology slide using whole slide color normalization and down-sampling, and at least one patch extraction routine, wherein the at least one patch extraction routine comprises using a sliding window to extract patches of the preprocessed stained histopathology slide;
    extracting texture features from the annotated image;
    determining a distribution of the extracted texture features relative to tissue conditions, wherein the determining step comprises quantifying the distribution of the extracted texture features within the annotated entire image and quantifying spatial relationships relative to the tissue conditions of the tissue structures;
    classifying the patient into a risk group based on the determining step; and
    treating the patient accordingly based on the risk group.

2. The method of claim 1, wherein the annotating comprises:
    color deconvoluting each of the plurality of patches to a plurality of stain layers;
    extracting a plurality of texture features from the plurality of patches;
    inputting the extracted texture features into a random forest to output a probability of each patch belonging to a category of tissue structure; and
    combining the patch probabilities to form an image annotation of tissue structures.

3. The method of claim 2, wherein the plurality of texture features comprise at least one selected texture feature, at least one convolutional neural network fully connected terminal layer features, or a combination of the two.

4. The method of claim 3, wherein the determining the distribution comprises determining feature distributions, spatial features which compare distances between different tissue regions, and region confidence.

5. The method of claim 4, wherein the classifying comprises:
    selecting a plurality of features; and
    inputting the selected features into at least one machine learning process to output a probability of a condition to be treated and a treatment recommendation.

6. The method of claim 1, wherein the living tissue is breast tissue and the risk groups relate to risk of recurrence of breast cancer.

7. The method of claim 6, wherein the breast cancer is ductal carcinoma in situ.

8. The method of claim 7, wherein the categories of tissue structure comprise malignant duct, immune rich stroma, non-immune rich stroma, non-cancerous duct, and blood vessel.

9. A system for detecting malicious email messages, the system comprising a processor, memory accessible by the processor, and computer program instructions stored in the memory and executable by the processor to perform:
    receiving an image of living tissue of a patient, the image comprising a stained histopathology slide;
    annotating, via a whole slide annotation routine, the entire image into tissue structures, wherein the whole slide annotation routine includes at least one preprocessing routing to preprocess the stained histopathology slide using whole slide color normalization and down-sampling, and at least one patch extraction routine, wherein the at least one patch extraction routine comprises using a sliding window to extract patches of the preprocessed stained histopathology slide;
    extracting texture features from the annotated image;
    determining a distribution of the extracted texture features relative to tissue conditions, wherein the determining step comprises quantifying the distribution of the extracted texture features within the annotated entire image and quantifying spatial relationships relative to the tissue conditions of the tissue structures;
    classifying the patient into a risk group based on the determining step; and
    treating the patient accordingly based on the risk group.

10. The system of claim 9, wherein the annotating comprises:
    color deconvoluting each of the plurality of patches to a plurality of stain layers;
    extracting a plurality of texture features from the plurality of patches;
    inputting the extracted texture features into a random forest to output a probability of each patch belonging to a category of tissue structure; and
    combining the patch probabilities to form an image annotation of tissue structures.

11. The system of claim 10, wherein the plurality of texture features comprise at least one selected texture feature, at least one convolutional neural network fully connected terminal layer features, or a combination of the two.

12. The system of claim 11, wherein the determining the distribution comprises determining feature distributions, spatial features which compare distances between different tissue regions, and region confidence.

13. The system of claim 12, wherein the classifying comprises:
    selecting a plurality of features; and
    inputting the selected features into at least one machine learning process to output a probability of a condition to be treated and a treatment recommendation.

14. The system of claim 9, wherein the living tissue is breast tissue and the risk groups relate to risk of recurrence of breast cancer.

15. The system of claim 14, wherein the breast cancer is ductal carcinoma in situ.

16. The system of claim 15, wherein the categories of tissue structure comprise malignant duct, immune rich stroma, non-immune rich stroma, non-cancerous duct, and blood vessel.

17. A computer program product for detecting malicious email messages, the computer program product comprising a non-transitory computer readable storage having program instructions embodied therewith, the program instructions executable by a computer, to cause the computer to perform a method comprising:
    receiving an image of living tissue of a patient, the image comprising a stained histopathology slide;
    annotating, via a whole slide annotation routine, the entire image into tissue structures, wherein the whole slide annotation routine includes at least one preprocessing routing to preprocess the stained histopathology slide using whole slide color normalization and down-sampling, and at least one patch extraction routine, wherein the at least one patch extraction routine comprises using a sliding window to extract patches of the preprocessed stained histopathology slide;

extracting texture features from the annotated image;

determining a distribution of the extracted texture features relative to tissue conditions, wherein the determining step comprises quantifying the distribution of the extracted texture features within the annotated entire image and quantifying spatial relationships relative to the tissue conditions of the tissue structures;

classifying the patient into a risk group based on the determining step; and treating the patient accordingly based on the risk group.

18. The computer program product of claim 17, wherein the annotating comprises:

color deconvoluting each of the plurality of patches to a plurality of stain layers;

extracting a plurality of texture features from the plurality of patches;

inputting the extracted texture features into a random forest to output a probability of each patch belonging to a category of tissue structure; and combining the patch probabilities to form an image annotation of tissue structures.

19. The computer program product of claim 18, wherein the plurality of texture features comprise at least one selected texture feature, at least one convolutional neural network fully connected terminal layer features, or a combination of the two.

20. The computer program product of claim 19, wherein the determining the distribution comprises determining feature distributions, spatial features which compare distances between different tissue regions, and region confidence.

21. The computer program product of claim 20, wherein the classifying comprises:

selecting a plurality of features; and inputting the selected features into at least one machine learning process to output a probability of a condition to be treated and a treatment recommendation.

22. The computer program product of claim 17, wherein the living tissue is breast tissue and the risk groups relate to risk of recurrence of breast cancer.

23. The computer program product of claim 22, wherein the breast cancer is ductal carcinoma in situ.

24. The computer program product of claim 23, wherein the categories of tissue structure comprise malignant duct, immune rich stroma, non-immune rich stroma, non-cancerous duct, and blood vessel.

* * * * *